US009132197B2

(12) United States Patent
Kaplan et al.

(10) Patent No.: US 9,132,197 B2
(45) Date of Patent: Sep. 15, 2015

(54) SILK FIBROIN MATERIALS AND USE THEREOF

(71) Applicants: Trustees of Tufts College, Medford, MA (US); MASSACHUSETTS INSTITUTE OF TECHNOLOGY, Cambridge, MA (US)

(72) Inventors: David L. Kaplan, Concord, MA (US); Rina Nazarov, Pine Meadow, CT (US); Gordana Vunjak-Novakovic, New York, NY (US); Lorenz Meinel, Niestetal (DE)

(73) Assignees: Massachusetts Institute of Technology, Cambridge, MA (US); Trustees of Tufts College, Medford, MA (US)

( * ) Notice: Subject to any disclaimer, the term of this patent is extended or adjusted under 35 U.S.C. 154(b) by 0 days.

(21) Appl. No.: 13/767,190

(22) Filed: Feb. 14, 2013

(65) Prior Publication Data

US 2013/0158131 A1  Jun. 20, 2013

Related U.S. Application Data

(63) Continuation of application No. 13/680,570, filed on Nov. 19, 2012, which is a continuation of application No. 12/836,692, filed on Jul. 15, 2010, now Pat. No. 8,361,617, which is a continuation of application No. 10/541,182, filed as application No. PCT/US2004/000255 on Jan. 7, 2004, now Pat. No. 7,842,780.

(60) Provisional application No. 60/438,393, filed on Jan. 7, 2003.

(51) Int. Cl.
*A61K 38/17* (2006.01)
*A61K 47/42* (2006.01)
*A61L 27/22* (2006.01)
*A61L 27/26* (2006.01)
*A61L 27/36* (2006.01)
*A61L 27/38* (2006.01)
*A61L 27/56* (2006.01)
*D01D 5/00* (2006.01)
*D01F 4/02* (2006.01)
*A61K 38/18* (2006.01)

(52) U.S. Cl.
CPC ............ *A61K 47/42* (2013.01); *A61K 38/1825* (2013.01); *A61K 38/1841* (2013.01); *A61L 27/227* (2013.01); *A61L 27/26* (2013.01); *A61L 27/3604* (2013.01); *A61L 27/3847* (2013.01); *A61L 27/3852* (2013.01); *A61L 27/3895* (2013.01); *A61L 27/56* (2013.01); *D01D 5/00* (2013.01); *D01F 4/02* (2013.01); *Y10T 428/29* (2013.01)

(58) Field of Classification Search
USPC ........................................................ 530/353
See application file for complete search history.

(56) References Cited

U.S. PATENT DOCUMENTS

| | | | |
|---|---|---|---|
| 1,989,005 | A | 1/1935 | Fink et al. |
| 4,233,212 | A | 11/1980 | Otoi et al. |
| 4,820,418 | A | 4/1989 | Hirotsu et al. |
| 5,047,507 | A | 9/1991 | Buchegger et al. |
| 5,171,505 | A | 12/1992 | Lock |
| 5,252,285 | A | 10/1993 | Lock |
| 5,290,494 | A | 3/1994 | Coombes et al. |
| 5,606,019 | A | 2/1997 | Cappello |
| 5,728,810 | A | 3/1998 | Lewis et al. |
| 5,736,188 | A | 4/1998 | Alcock et al. |
| 5,770,193 | A | 6/1998 | Vacanti et al. |
| 5,994,099 | A | 11/1999 | Lewis et al. |
| 6,110,590 | A | 8/2000 | Zarkoob et al. |
| 6,123,819 | A | 9/2000 | Peeters |
| 6,175,053 | B1 | 1/2001 | Tsubouchi |
| 6,592,623 | B1 | 7/2003 | Bowlin et al. |
| 6,815,427 | B2 | 11/2004 | Tsubouchi et al. |
| 6,902,932 | B2 | 6/2005 | Altman et al. |
| 7,041,797 | B2 | 5/2006 | Vollrath |
| 7,057,023 | B2 | 6/2006 | Islam et al. |
| 7,285,637 | B2 | 10/2007 | Armato et al. |
| 7,635,755 | B2 | 12/2009 | Kaplan et al. |
| 7,662,409 | B2 | 2/2010 | Masters |
| 7,674,882 | B2 | 3/2010 | Kaplan et al. |

(Continued)

FOREIGN PATENT DOCUMENTS

CA 2405850 A1 10/2002
EP 1440088 A2 7/2004

(Continued)

OTHER PUBLICATIONS

Li et al. 2001. Study on Porous Silk Fibroin Materials. I. Fine Structure of Freeze Dried Silk Fibroin. Journal of Applied Polymer Science, 2001vol. 79, pp. 2185-2191.*
D.J. Mooney et al. 1996. Novel approach to fabricate porous sponges of poly D, L-lactic-co-glycolic acid without the use of organic solvents, Biomaterials, vol. 17, pp. 1417-1422.*
Anthanasiou et al., Biomaterials, 17:93-102 (1996). "Sterilization, toxicity, biocompatibility and clinical applications of polylactic acid/polyglocolic acid copolymers."

(Continued)

*Primary Examiner* — Debbie K Ware
*Assistant Examiner* — Kailash C Srivastava
(74) *Attorney, Agent, or Firm* — Choate, Hall & Stewart, LLP

(57) ABSTRACT

The present invention provides processes for producing porous silk fibroin scaffold material. The porous silk fibroin scaffold can be used for tissue engineering. The porosity of the silk fibroin scaffolds described herein can be adjusted as to mimic the gradient of densities found in natural tissue. Accordingly, methods for engineering of 3-dimensional tissue, e.g. bone and cartilage, using the silk fibroin scaffold material are also provided.

8 Claims, 16 Drawing Sheets

(56) References Cited

U.S. PATENT DOCUMENTS

| | | | |
|---|---|---|---|
| 7,727,575 | B2 | 6/2010 | Kaplan et al. |
| 7,842,780 | B2 | 11/2010 | Kaplan et al. |
| 7,960,509 | B2 | 6/2011 | Kaplan et al. |
| 8,071,722 | B2 | 12/2011 | Kaplan et al. |
| 8,361,617 | B2 | 1/2013 | Kaplan et al. |
| 2002/0028243 | A1 | 3/2002 | Masters |
| 2003/0007991 | A1 | 1/2003 | Masters |
| 2003/0183978 | A1 | 10/2003 | Asakura |
| 2004/0005363 | A1 | 1/2004 | Tsukada et al. |
| 2004/0224406 | A1 | 11/2004 | Altman et al. |
| 2004/0266992 | A1 | 12/2004 | Migliaresi et al. |
| 2007/0212730 | A1 | 9/2007 | Vepari et al. |
| 2008/0085272 | A1 | 4/2008 | Kaplan et al. |
| 2008/0293919 | A1 | 11/2008 | Kaplan et al. |
| 2009/0202614 | A1 | 8/2009 | Kaplan et al. |
| 2009/0232963 | A1 | 9/2009 | Kaplan et al. |
| 2009/0234026 | A1 | 9/2009 | Kaplan et al. |
| 2010/0028451 | A1 | 2/2010 | Kaplan et al. |
| 2010/0046902 | A1 | 2/2010 | Kaplan et al. |
| 2010/0055438 | A1 | 3/2010 | Kaplan et al. |
| 2010/0063404 | A1 | 3/2010 | Kaplan et al. |
| 2010/0065784 | A1 | 3/2010 | Kaplan et al. |
| 2010/0068740 | A1 | 3/2010 | Kaplan et al. |
| 2010/0070068 | A1 | 3/2010 | Kaplan et al. |
| 2010/0096763 | A1 | 4/2010 | Kaplan et al. |
| 2010/0120116 | A1 | 5/2010 | Kaplan et al. |
| 2010/0178304 | A1 | 7/2010 | Wang et al. |
| 2010/0191328 | A1 | 7/2010 | Kaplan et al. |
| 2010/0196447 | A1 | 8/2010 | Kaplan et al. |
| 2011/0046686 | A1 | 2/2011 | Kaplan et al. |
| 2011/0076384 | A1 | 3/2011 | Cannizzaro et al. |
| 2011/0135697 | A1 | 6/2011 | Omenetto et al. |
| 2011/0152214 | A1 | 6/2011 | Boison et al. |
| 2011/0171239 | A1 | 7/2011 | Kaplan et al. |
| 2012/0121820 | A1 | 5/2012 | Kaplan et al. |
| 2012/0123519 | A1 | 5/2012 | Lovett et al. |
| 2014/0094410 | A1 | 4/2014 | Kaplan et al. |

FOREIGN PATENT DOCUMENTS

| | | |
|---|---|---|
| GB | 1182153 A | 2/1970 |
| JP | 55-139427 | 10/1930 |
| JP | 60142259 A | 7/1985 |
| JP | 60-259677 | 12/1985 |
| JP | 01118544 | 11/1989 |
| JP | H06-346314 A | 12/1994 |
| JP | 08-295697 | 11/1996 |
| JP | 10-36676 | 2/1998 |
| JP | 2000-273264 A | 10/2000 |
| JP | 2003/192807 A | 7/2003 |
| JP | 2004-068161 A | 3/2004 |
| WO | WO-99/01089 A1 | 1/1999 |
| WO | WO-01/36531 A1 | 5/2001 |
| WO | 01/54667 A1 | 8/2001 |
| WO | WO-01/56626 A1 | 8/2001 |
| WO | 01/80921 A2 | 11/2001 |
| WO | WO-02/29141 A1 | 4/2002 |
| WO | WO-02/072931 A1 | 9/2002 |
| WO | WO-03/022909 A1 | 3/2003 |
| WO | WO-03/038033 A2 | 5/2003 |
| WO | WO-2004/000915 A2 | 12/2003 |
| WO | WO-2004/041845 A2 | 5/2004 |
| WO | WO-2005/123114 A2 | 12/2005 |
| WO | WO-2008127405 A2 | 10/2008 |
| WO | WO-2011/006133 A2 | 1/2011 |

OTHER PUBLICATIONS

Asakura, T., Bioindustry, 4(11):36-44 (1987), Translated pp. 1-24. Translated title: "Structural characteristics of silk fibroin and its application to enzyme fixation material."
Bognitzki et al., Adv Mater, 13(1):70-72 (2001). "Nanostructured fibers via electrospinning."
Boland et al., Polymeric Materials: Science & Engineering, 85:51-52 (2001). "Electrospinning of tissue engineering scaffolds."
Caterson et al., Biomed Mater Res, 57:394-403 (2001). "Three-dimensional cartilage formulation by bone marrow-derived cells seeded in polylactide/alginate amalgam."
Dal Pra et al., Tissue Engineering, 9(6):1113-1121 (2003). "Silk fibron-coated three-dimensional polyurethane scaffolds for tissue engineering: interactions with normal human fibroblasts."
Demura et al., Biosensors, 361-372 (1989). "Immobilization of biocatalysts with *Bombyx mori* silk fibroin by several kinds of physical treatment and its application to glucose sensors."
Doshi et al., Journal of Electrostatics, 35:151-160 (1995). "Electronspinning process and applications of electrospun fibers."
Elcin et al., Artificial Cells Blood Substitutes and Immobilization Biotechnology, 24(3):257-71 (1996). "Controlled release of endothelial cell growth factor from chitosan-albumin microspheres for localized angiogenesis: in vitro and in vivo studies."
Holy et al., J Biomed Mater Res. 65A:447-453 (2003). "Use of a biomimetic strategy to engineer one."
Hutmacher, Biomaterials, 21:2529-2543 (2000). "Scaffolds in tissue engineering bone and cartilage."
Jin et al., Polymer Preprints (American Chemical Society, Division of Polymer Chemistry) 43(2):743-744 (2002).
Karp et al., The Journal of Craniofacial Surgery, 14(3):317-323 (2003). "Fabrication of precise cylindrical three-dimensional tissue engineering scaffolds for in vitro and in vivo bone engineering applications."
Li et al., J Appl Polym Sci, 79:2185-2191 (2001). "Study on porous silk fibroin materials. I. Fine structure of freeze dried silk fibroin."
Li et al., Polymer Adv Technology, 13:605-610 (2002). "Study on porous fibroin materials: 3. Influence of repeated free-thawing on the structure and properties of porous silk fibroin materials."
Martin et al., J Biomed Mater Res, 55:229-235 (2001). "Selective differentiation of mammalian bone marrow stromal cells cultured on three-dimensional polymer foams."
Nam et al., J Appl Polym Sci, 81:3008-3021 (2001). "Morphology of regenerated silk fibroin: effects of freezing temperature, alcohol addition, and molecular weight."
Ohgushi et al., CRD Handbook of Bioactive Ceramics, vol. II: 235-238. "Calcium phosphate block ceramic with bone marrow cells in a rat long bone defect."
Perez-Rigueiro, J Appl Plym Sci, 70:2439-2447 (1998). "Silkworm silk as an engineering material."
Petite et al., Nature Biotechnology, 18:959-963 (2000). "Tissue-engineered bone regeneration."
Sofia et al., J Biomed Mater Res, 14:139-148(2000). "Functionalized silk-based biomaterials for bone formation."
Stitzel et al., J Biomater Appl, 16:22-23 (2001). "Aterial smooth muscle cell proliferation on a novel biomimicking, biodegradable vascular graft scaffold."
Tsukada et al., Journal of Applied Polymer Science, 54:507-514 (1994). "Preparation and application of porous silk fibroin materials."
Zarkoob, A Dissertation Presented to The Graduate Faculty of the University of Akron, Aug. 1998. "Structure and morphology of regenerated silk nano-fibers produced by electrospinning."
Zarkoob, Polymer Preprints (American Chemical Society, Division of Polymer Chemistry), 39(2):244-245 (1998). "Structure and morphology of nano electrospun silk fibers."
Wang et al., Biomaterial Coatings by Stepwise Deposition of Silk Fibroin, Langmuir, 21:11335-11341 (2005).
Database WPI Week 198205, Derwent Publications Ltd., London, GB: AN 1982-09092E & JP 56 166235 A, Abstract (Dec. 21, 1981).
Asakura et al., Conformational characterization of *B. mori* silk fibroin in the solid state by high-frequency 13C cross polarization magic angle spinning NMR, X-ray diffraction and infrared spectroscopy, Macromolecules 18:1841-1845 (1985).
Asakura et al., NMR of silk fibroin 2. C NMR study of the chain dynamics and solution structure of *Bombyx mori* silk fibroin Macromolecules. 17:1075-1081 (1984).
Chen et al., Separation of alcohol-water mixture by pervaporation through a novel natural polymer blend membrane-chitosan/silk fibroin blend membrane, J Appl Polymer Sci, 73:975-980 (1999).
Freddi et al., Silk fibroin/cellulose blend films: preparation, structure, and physical properties, J Appl Polymer Sci, 56:1537-1545 (1995).

References Cited

OTHER PUBLICATIONS

Reneker D.H. and Chun, I., Nanometre diameter fibres of polymer, produced by electrospinning, Nanotechnology 7:216-223 (1996).

Petrini et al., Silk fibroin-polyurethane scaffolds for tissue engineering, Journal of Materials Science: Materials in Medicine, 12:849-853 (2001).

Yamada et al., AFM observation of silk fibroin on mica substrates: morphologies reflecting the secondary structure, Thin Solid Films 440:208-216 (2003).

Zhou et al., Preparation of a novel core-shell nanostructured gold colloid-silk fibroin bioconjugate by the protein in situ redox technique at room temperature, Chem Commun, 2518-2519 (2001).

Sawyer et al., Dextran therapy in thrombophlebitis. Abstract, JAMA, 191(9):740-742 (1965).

Hijirida et al., 13C NMR of *Nephila clavipes* Marjo Ampullate Silk Gland, Biophysical Journal 71:3442-3447 (1996).

Megeed et al., Controlled Release of Plasmid DNA from a Genetically Engineered Silk-Elastin like Hydrogel, Pharmaceutical Research, 19(7):954-959 (2002).

Hinman et al., Synthetic spider silk: a modular fiber, TIBTECH 18:374-379 (2000).

Huang et al., Generation of Synthetic Elastin-Mimetic Small Diameter Fibers and Fiber Networks, Macromolecules. 33:2989-2997 (2000).

Huang et al., Engineered collagen-PEO nanofibers and fabrics, J Biomater Sci Polymer Edn, 12(9):979-993 (2001).

Kweon et al., Preparation of Semi-interpreting Polymer Networks Composed of Silk Fibroin and Poly( ethylene glycol) Macromer, J. Appl Polymer Sci, 80: 1848-1853 (2001).

Lazaris et al., Spider silk fibers spun from soluble recombinant silk produced in mammalian cells, Science, 295: 472-476 (2002).

Liang et al., Improvements of the Physical Properties of Fibroin Membranes with Sodium Alginate, J. Appl Polymer Sci, 45:1937-1943 (1992).

Chen, X. et al., Conformation Transition Kinetics of *Bombyx mori* Silk Protein, Proteins: Structure, Function, and Bioinformatics 68:223-231 (2007).

Chen et al., pH Sensitivity and Ion Sensitivity of Hydrogels Based on Complex-Forming Chitosan/Silk Fibroin Interpenetrating Polymer Network, J Appl Polymer Sci, 65:2257-2262 (1997).

Asakura, T., Porous membrane of *Bombyx mori* silk fibroin: structure characterization, physical properties and application to glucose oxidase immobilization, Journal of Membrane Science, 59:39-52 (1991).

Demura, M., Porous membrane of *Bombyx mori* silk fibroin: structure characterization, physical properties and application to glucose oxidase immobilization, Journal of Membrane Science, 59:32-52 (1991).

Book (Proteins: Three Dimensional Structure, Chapter 6, pp. 124-160).

Claria et al., Aspirin triggers previously undescribed bioactive eicosanoids by human endothelial cell-leukocyte interactions, Proceedings of the National Academy of Sciences USA, 92:9475-9479 (1995).

Tamada, Modification of Fibroin Film with a Chimera Fibroin Fragment for Improvement Cell Adhesion, The 1998 MRS Symposium, San Francisco, CA, USA, Apr. 13-14, 1998, 530:27-32 (1998).

* cited by examiner

COLLAGEN

SILK

COLLAGEN

SILK

COLLAGEN

SILK

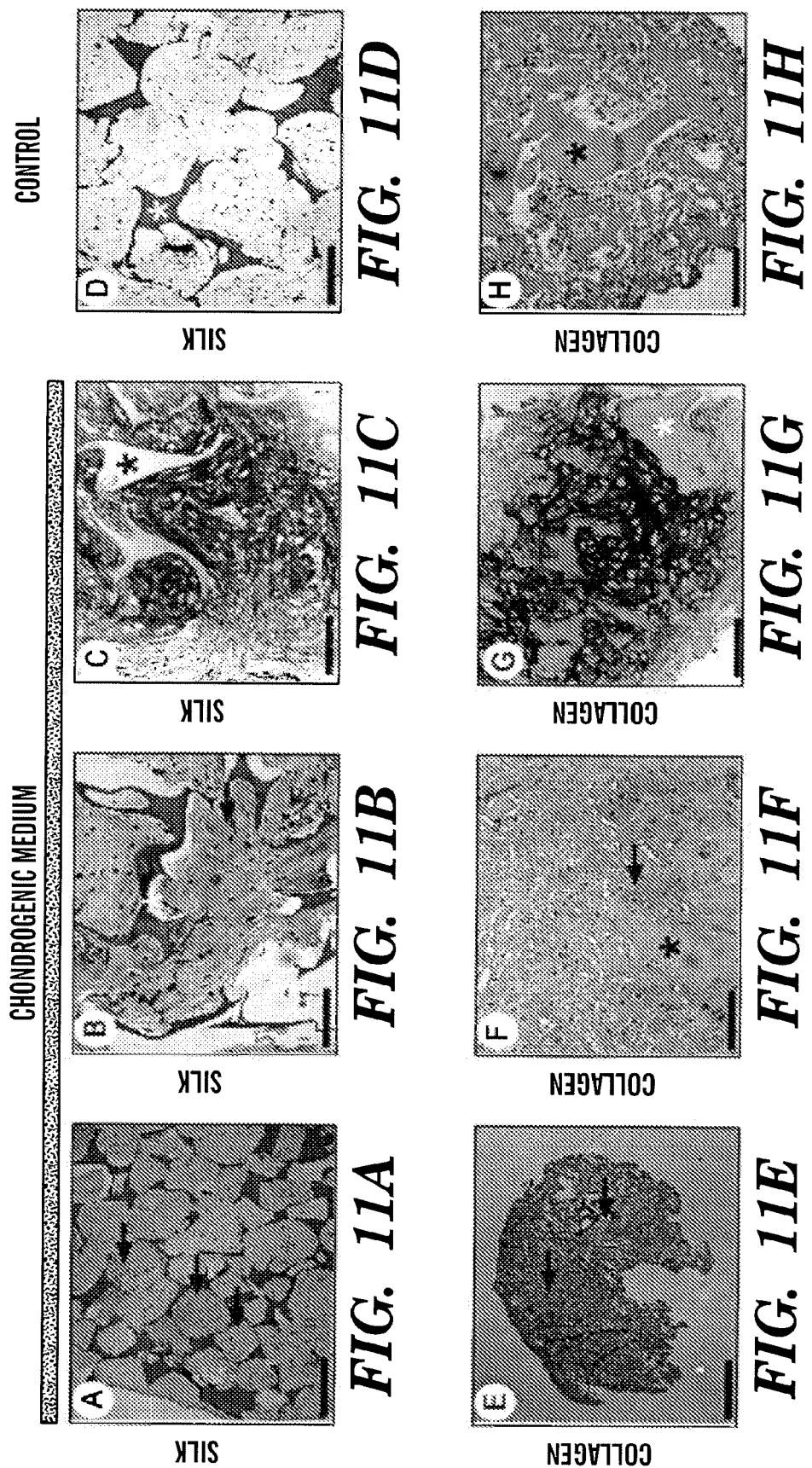

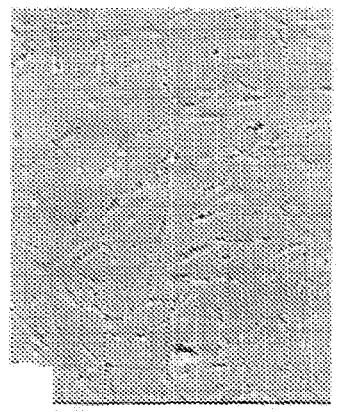
FIG. 12A
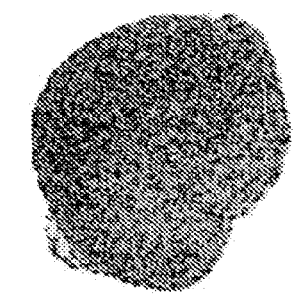
FIG. 12B
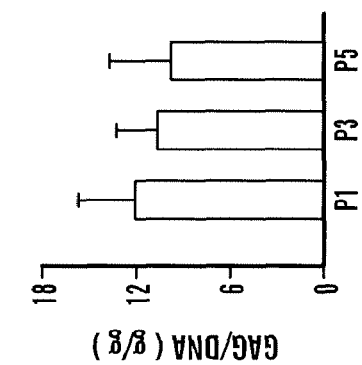
FIG. 12C
FIG. 12D
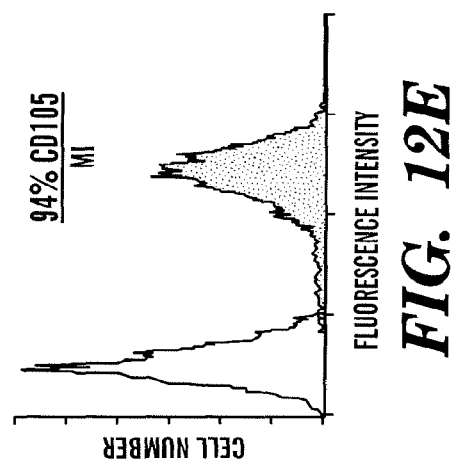
FIG. 12E
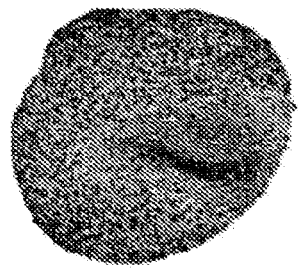
FIG. 12F
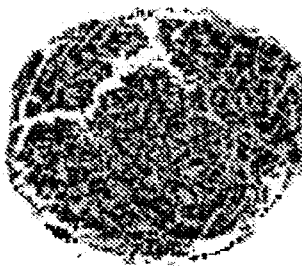
FIG. 12G
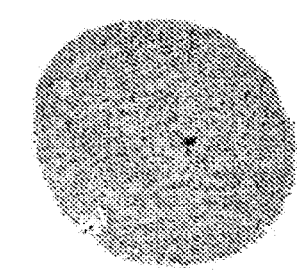
FIG. 12H

SILK FIBROIN MATERIALS AND USE THEREOF

CROSS REFERENCE TO RELATED APPLICATIONS

This application is a continuation application of U.S. patent application Ser. No. 13/680,570 filed on Nov. 19, 2012, which is a continuation application of U.S. patent application Ser. No. 12/836,692 filed on Jul. 15, 2010 and issued as U.S. Pat. No. 8,361,617 on Jan. 29, 2013, which is a continuation application of U.S. patent application Ser. No. 10/541,182 filed on Jun. 14, 2006 and issued as U.S. Pat. No. 7,842,780 on Nov. 30, 2010, which is a 35 U.S.C. §371 National Entry of International Application No. PCT/US04/00255 filed on Jan. 7, 2004, which claims benefit under 35 U.S.C. 119(e) of U.S. Provisional Application No. 60/438,393 filed on Jan. 7, 2003, the contents of each of which are incorporated herein by reference in their entireties.

GOVERNMENT SUPPORT

This invention was made with United States Government support under Grant No. 1R01DE13405-01A1 awarded by the National Institutes of Health, and Grant No. DMR-0090384 awarded by the National Science Foundation. The United States Government has certain rights in the invention.

FIELD OF THE INVENTION

The present invention provides methods for the production of 3-dimensional porous silk fibroin scaffolds that can be used in tissue engineering. The silk fibroin scaffolds described herein are particularly suited for tissue engineering as the porosity of the scaffold can be adjusted throughout mimicking the gradient of densities found in natural tissue. Methods for producing 3-dimensional tissue using the silk based scaffolds are also provided.

BACKGROUND OF THE INVENTION

A major goal of tissue engineering is to develop a biological alternative in vitro for regenerative tissue growth in vivo within a defect area. Porous polymer scaffolds play a crucial role in the three-dimensional growth and formation of new tissue in the field of tissue engineering.

In recent years biodegradable polymers such as poly (glycolic acid), poly (L-lactic acid) (PLLA) and their copolymers poly(L-lactic-co-glycolic acid) (PLGA) have been used as scaffold materials in studies of tissue formation. (Sofia et al. *Journal of Biomedical materials research* 2001, 54, 139-148). The advantages of these polymers is their biocompatibility and degradability. However, PLGA can induce inflammation due to the acid degradation products that result during hydrolysis (Sofia et al. *Journal of Biomedical materials research* 2001, 54, 139-148). There also are processing difficulties with polyesters that can lead to inconsistent hydrolysis rates and tissue response profiles. Thus, there is a need for polymeric materials that have more controllable features such as hydrolysis rates, structure, and mechanical strength, while also being biodegradable and biocompatible. Biological polymeric materials often demonstrate combinations of properties which are unable to be reproduced by synthetic polymeric materials. (Perez-Rigueiro et al. *Science*, 1998; 70: 2439-2447; Hutmacher D. *Biomaterials* 2000. 21, 2529-2543). Bone tissue is one example; scaffolds for bone tissue regeneration require high mechanical strength and porosity along with biodegradability and biocompatibility.

Several studies have shown that BMSCs can differentiate along an osteogenic lineage and form three-dimensional bone-like tissue (Holy et al. J. Biomed. Mater. Res. (2003) 65A:447-453; Karp et al., J. Craniofacial Surgery 14(3): 317-323). However, there are important limitations. Some calcium phosphate scaffolds show limited ability to degrade (Ohgushi et al. 1992. In *CRC Handbook of bioactive ceramics*. T. Yamamuro, L. L. Hench, and J. Wilson, editors. Boca Raton, Fla.: CRC Press. 235-238), or degradation is too rapid (Petite et al. 2000. *Nat Biotechnol* 18:959-963.) Polymeric scaffolds used for bone tissue engineering, such as poly(lactic-co-glycolic acid) or poly-L-lactic acid can induce inflammation due to acid hydrolysis products, and processing difficulties can lead to inconsistent hydrolysis rates and tissue response profiles (Athanasiou, et al. 1996. *Biomaterials* 17:93-102; Hollinger et al. 1996. *Clin Orthop:*55-65). Difficulties in matching mechanical properties to support desired function also remain an issue (Harris et al. *J Biomed Mater Res* 42:396-402).

Studies have also shown that BMSCs can differentiate along chondrogenic lineage and form three-dimensional cartilage-like tissue on biomaterial substrates, such as poly(lactic-co-glycolic acid) or poly-L-lactic acid (Caterson et al. 2001. *J Biomed Mater Res* 57:394-403; Martin et al. 2001. *J Biomed Mater Res* 55:229-235). However, the use of these scaffolds for cartilage formation present with the same limitations as observed with their use in bone engineering.

Therefore, in light of the disadvantages in the existing polymers, and even for more diverse options in degradable polymer systems, there exists a need for additional biocompatible polymers, particularly polymers suitable for formation of scaffolds for mechanically robust applications such as bone or cartilage. The fabrication process for such scaffolds should be simple, reproducible, and the variables relatively easy to control in order to consistently modulate mechanical properties and porosity without sacrificing biodegradation.

SUMMARY OF THE INVENTION

The present invention relates to a porous silk fibroin material comprising a three-dimensional silk fibroin body having interconnected pores therein. The pores having a diameter of 50 to 1000 microns. The pore density is from 20-200 mg/ml, preferably from 40-150 mg/ml. Porosity ranges from 50-99.5%, preferably 70-99%. Most preferably the porosity is above 80%. The density or porosity can be adjusted depending on the use of material.

Preferably, the material has a compressive modulus of at least 100 kPa. More preferably, the material has a compressive modulus of at least 150 kPa. Even more preferably, the material has a compressive modulus of 200 kPa. Most preferably, the material has a compressive modulus of 250 kPa.

The porous silk fibroin material of the invention can be used, for example, as a scaffold for a engineered tissue or as a drug delivery device. In tissue engineering, the porosity of the scaffold can be adjusted as to mimic the gradient of cellular densities found in natural tissue. As such, an organized three-dimensional tissue with a shape and cellular organization substantially similar to that of the tissue in vivo is produced.

In one preferred embodiment, a porous silk fibroin material is produced by a process comprising the steps of: (a) forming a silk fibroin solution comprising silk fibroin in an aqueous salt solution; (b) removing the salt and water from the fibroin solution to form a silk fibroin substance; (c) forming a polymer solution comprising about 5 to 35% by weight of the silk fibroin substance in a solvent; (d) contacting the polymer solution with water-soluble non-toxic particles that are insoluble in organic solvents and have a diameter between about 50 and about 1000 microns; (e) placing the polymer solution into a form; (f) removing the solvent from the polymer; (g) contacting said polymer solution with an effective amount of an agent to induce β-sheet structure and insolubility in aqueous solution; (h) leaching said polymer with a solvent in which said particles are soluble and polymer is insoluble to remove said particles from said polymer; and (i) drying said polymer.

Preferably, the solvent in step (c) is selected from the group consisting of hexa-fluoro-iso-propanol (HFIP), N-methyl morpholine N-oxide and calcium nitrate-methanol. Most preferably the solvent is hexa-fluoro-iso-propanol (HFIP).

Preferably the solvent is removed from the polymer by sublimination or evaporation.

In another embodiment, the agent to induce β-sheet structure is an alcohol and is selected from the group consisting of methanol, 2-propanol, or 1-butanol, isoamyl alcohol. The agent may also be a solvent such as chloroform or acetone.

In yet another embodiment, the aqueous salt solution comprises lithium bromide, lithium thiocyanate, calcium nitrate or related chemicals that solubilize the silk.

In one embodiment, the particles are selected from the group consisting of alkali metal and alkaline earth metal halides, phosphates and sulfates, sugar crystals, water-soluble polymer microspheres, polysaccharides and protein microspheres.

In a preferred embodiment, the particles are sodium chloride crystals.

In one embodiment, the polymer used in the method is leached with water.

The invention also provides a porous silk fibroin scaffold material prepared by the process for producing a porous silk as outlined above. The porous silk fibroin material may be combined with other biodegradable polymers.

In one embodiment, the pore density or porosity may be different within separate portions of the material. For example, by altering the size of the water-soluble particles placed in different positions in the mold, the pore density of the material can be controlled.

The present invention further provides for methods for the production of tissue both in vivo and ex vivo using the porous silk fibroin scaffolds described herein. Tissues include for example, cartilaginous and bone tissue.

In one embodiment, tissue is produced ex vivo by culturing mammalian cells on a porous silk fibroin scaffold under conditions that are appropriate for inducing the tissue formation. A bioreactor is preferably used.

In another embodiment, a method for producing tissue in vivo is provided. The method comprises seeding mammalian cells on a porous silk fibroin scaffold and implanting said scaffold into a patient.

In one aspect of the invention, the mammalian cells that are used for producing tissue are multipotent cells selected from the group consisting of bone marrow stromal cells and adult or embryonic stem cells. In one preferred embodiment, for production of bone tissue, the cells are bone marrow stromal cells.

In one preferred embodiment, the porous silk fibroin scaffold has a 3-dimensional structure of a predetermined shape such that the tissue produced takes the form of the 3-dimensional structure.

In one embodiment, the porous silk fibroin scaffold used in tissue engineering comprises silk fibroin selected from the group consisting of silks from silkworms, silks from spiders, silks from genetically engineered cells, silks from transgenic plants and animals, silks from cultured cells, native silk, silk from cloned full or partial sequences of native silk genes, and silk from synthetic genes encoding silk or silk-like sequences. Preferably fibroin obtained from *Bombyx mori* silkworms is used.

In one embodiment, the porous silk fibroin scaffold further comprises an additive. As used herein, an "additive" is any biologically or pharmaceutically active compound. Additives include, but are not limited to, peptides, antibodies, DNA, RNA, modified RNA/protein composites, glycogens or other sugars, and alcohols. In one preferred aspect the additive is a peptide that contains an integrin binding sequence, e.g. RGD. In another preferred aspect the additive is a growth factor.

In another embodiment, the porous silk fibroin scaffold further comprises one or more biodegradable polymers selected from the group consisting of collagens, polylactic acid or its copolymers, polyglycolic acid or its copolymers, polyanhydrides, elastin, glycosaminoclycans and polysaccharides.

In still another embodiment, the porous silk fibroin scaffold further comprises one or more non-biodegradable polymers selected from the group consisting of polyethylene, polystyrene, polymethylmethylcryalte, polyethylene oxide and polyurethanes.

In yet another embodiment, the porous silk fibroin scaffold further comprises an agent that enhances proliferation and/or differentiation of said mammalian cells.

In one embodiment, the cells used for tissue engineering are autologous cells; cells derived from the recipient of the bone or cartilage implant. Autologous cells can be animal cells, e.g. dog, cat, monkey, pig, cow, human, and the like. In one preferred embodiment, the autologous cells are human.

In another embodiment the cells used for tissue engineering are donor cells, derived from a source other than the recipient. In one aspect the donor cells are allogenic cells, i.e. from the same species as the recipient. In another aspect, the donor cells are derived from a different species than the recipient.

The present invention also provides 3-dimensional tissues produced using the porous silk fibroin material of the invention.

In yet another embodiment a method for treating a patient in need of an implant is provided. The method comprises implanting a 3-dimensional porous silk fibroin scaffold of predetermined shape. In one aspect, for example, the 3-dimensional porous silk fibroin scaffold of predetermined shape is implanted as a bone substitute or as a cartilage substitute. The 3-dimensional porous silk fibroin scaffold can be seeded with autologous or donor cells prior to implantation. Alternatively, the 3-dimensional porous silk fibroin scaffold can be implanted without seeding cells.

Unless otherwise defined, all technical and scientific terms used herein have the same meaning as commonly understood by one of ordinary skill in the art. Although methods and materials similar or equivalent to those described herein can be used in the practice or testing of the invention, the preferred methods and materials are described below. All publications, patent applications, patents and other references mentioned herein are incorporated by reference. In addition, the materials, methods and examples are illustrative only and not intended to be limiting. In case of conflict, the present specification, including definitions, controls.

BRIEF DESCRIPTION OF THE FIGURES

The accompanying figures, which are incorporated in and constitute a part of this specification, illustrate embodiments of the invention and, together with the description, serve to explain the objects, advantages, and principles of the invention.

FIGS. 11A-H show Safranin O staining of sections taken from scaffolds based on silk (11A, 11B, 11D) and collagen (11E, 11F, 11H) cultured in the presence of chondrogenic (11A-11D) and control media (11D, 11H) for 4 weeks. Asterisks indicate polymer, arrows chondrocytes. Immunohistochemistry using an antibody against type 2 collagen is shown in panel C and D. Bar=300 µm (11A, 11D) or 150 µm (11B-11D, 11F-11H).

FIGS. 12A-12H show characterization of BMSCs. (12A) phase-contrast photomicrographs of passage 2 BMSCs at an original magnification of ×20. (12B-12D) Characterization of chondrogenic differentiation in pellet culture. Pellets were either cultured in chondrogenic medium (12B) or control medium (12C). Pellet diameter is approximately 2 mm, and pellets were stained with safranin O/Fast Red. (12D) Sulphated GAG/DNA (µg/µg) deposition of passages 1, 3, and 5 BMSCs after 4 weeks. Data represents the average±standard deviation of 5 pellets. (B) Endoglin expression (CD105) of passage 2 BMSCs. (12F-12H) Characterization of osteoblastic differentiation along in pellet culture either treated in osteogenic (12F) or in control medium (12G) and stained according to von Kossa. Pellet diameter is approximately 2 mm. (12H) Calcium deposition/DNA (µg/ng) of passages 1, 3, and 5 BMSCs pellet culture. Passage 1 and 3 cells deposited significantly more calcium/DNA than passage 5 cells ($p<0.05$) and data represents the average±standard deviation of 5 pellets.

DETAILED DESCRIPTION OF THE INVENTION

Figure 1:
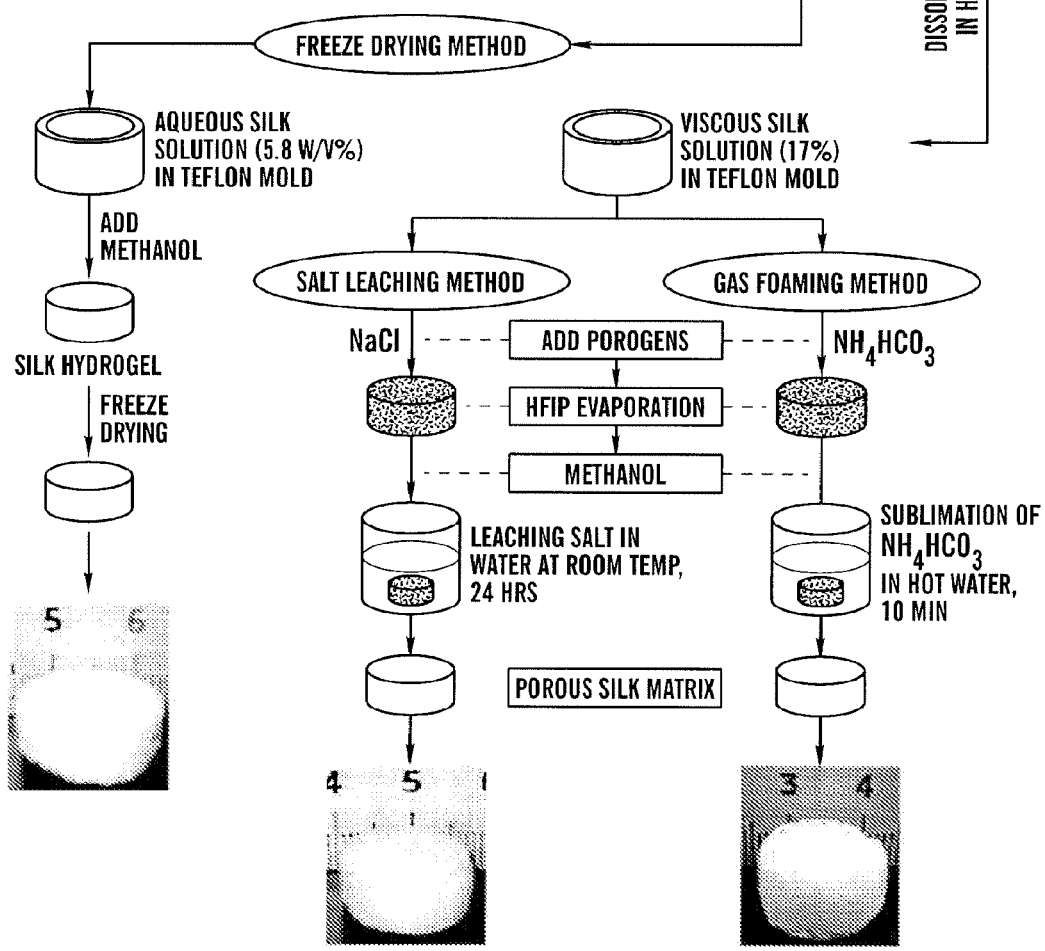
FIGS. 1A-B shows flow charts for silk processing (FIG. 1A) and silk fabrication (FIG. 1B).
Figure 2A:
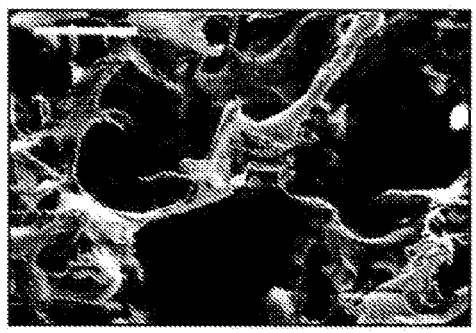
FIGS. 2A-F shows the SEM images of inner and outer structure silk scaffold formed by freeze drying: (2A) −20° C. in 15% methanol (inner) (scale bar; 50 µm), (2B) −20° C. in 15% methanol (outer) (scale bar; 50 µm), (2C) −20° C. in 15% 2-propanol (inner) (scale bar; 50 µm), (2D) −20° C. in 15% 2-propanol (outer) (scale bar; 50 µm), (2E) −80° C. in 15% methanol (inner) (scale bar; 100 µm) and (2F) −80° C. in 15% 2-propanol (inner) (scale bar; 100 µm). (Outer; outside image of the scaffolds, Inner; inside image of the scaffold after fracture in liquid nitrogen).
Figure 2B:
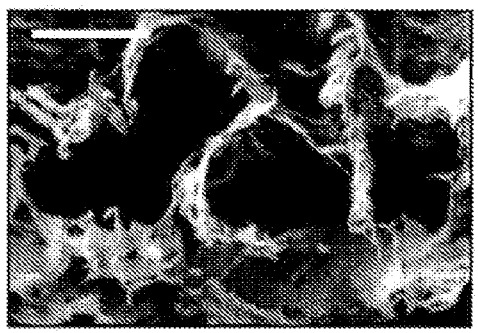
Figure 2C:
Figure 2D:
Figure 2E:
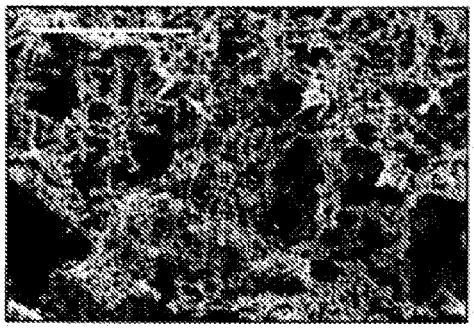
Figure 2F:
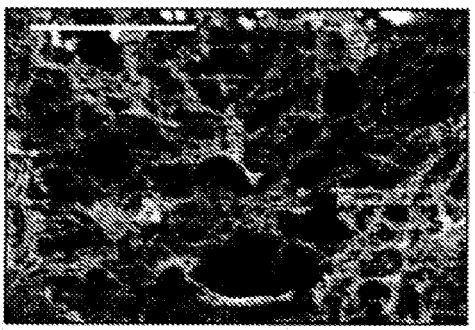
Figure 3A:
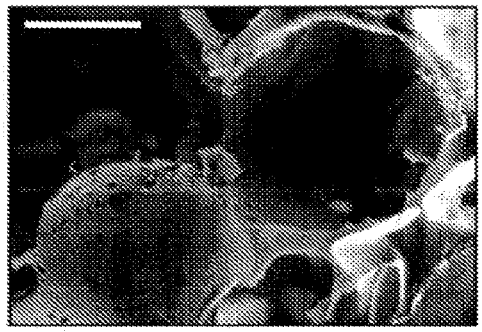
FIGS. 3A-D shows SEM images of inner and outer structure silk scaffold by salt leaching and gas foaming methods after methanol treatment (scale bar; 200 µm): (3A) NaCl:silk (10:1 wt %) (inner), (3B) NaCl:silk (10:1 wt %) (outer), (3C) $NH_4HCO_3$:silk (10:1 wt %) (inner) and (3D) $NH_4HCO_3$:silk (10:1 wt %) (outer).
Figure 3B:
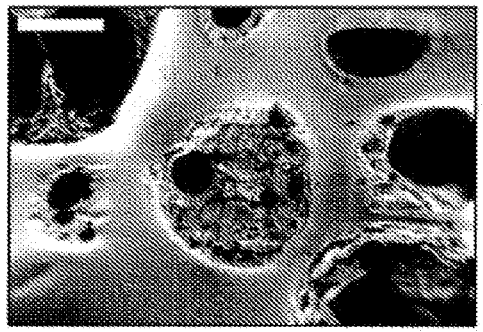
Figure 3C:
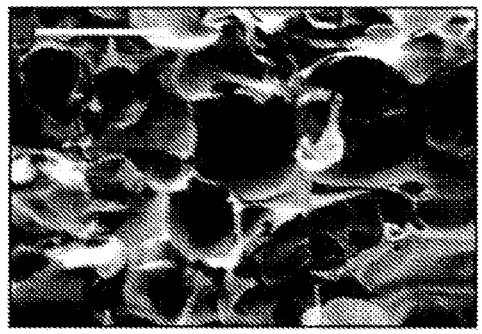
Figure 3D:
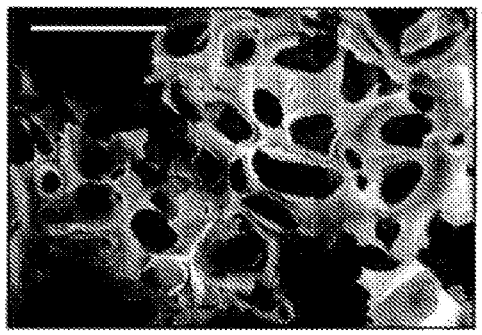
Figure 4A:
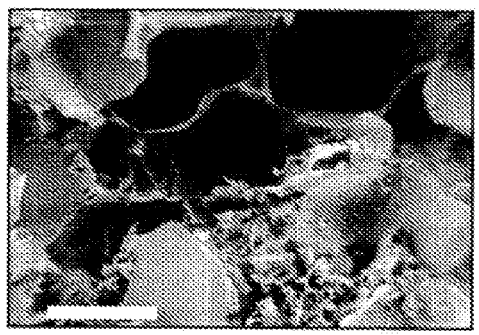
FIGS. 4A-E shows SEM images of silk scaffold by salt leaching and gas foaming methods after immersion in alcohols. (4A) salt leached scaffold immersed in methanol (scale bar; 200 µm), (4B) salt leached scaffold immersed in butanol (scale bar; 100 µm), (4C) gas foamed scaffold immersed in methanol (scale bar; 200 µm), (4D) gas foamed scaffold immersed in propanol (scale bar; 200 µm), (4E) gas foamed scaffold immersed in butanol (scale bar; 100 µm).
Figure 4B:
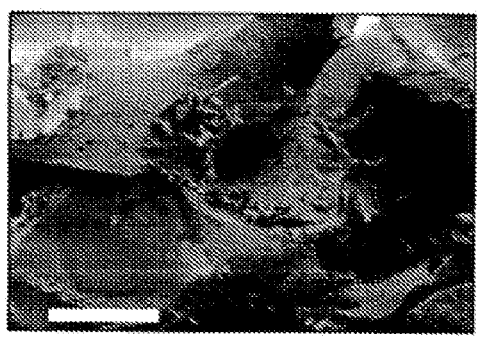
Figure 4C:
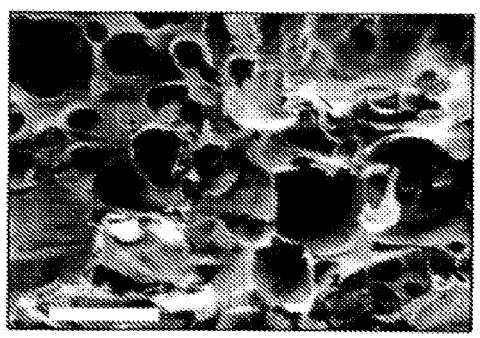
Figure 4D:
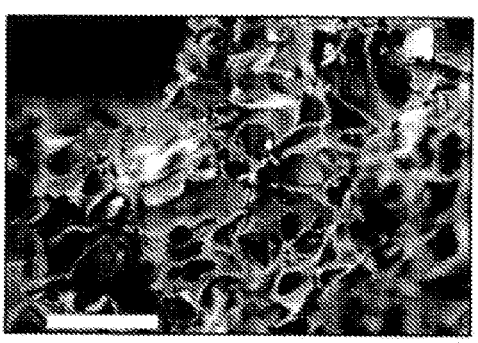
Figure 4E:
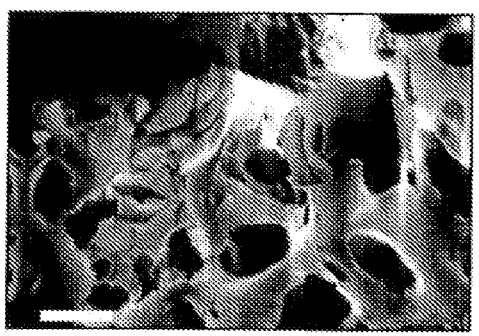

The invention is based upon a surprising finding that silk proteins processed into 3-dimensional architectures provides for suitable biomaterial and tissue engineering matrices. The present invention provides a porous silk fibroin material comprising a 3-dimensional silk fibroin body having pores with a diameter of 50 to 1000 microns. The pore density can be adjusted depending on the use of material.

The unique properties of silks (mechanical strength, slow biodegradability, biocompatibility, sequence variants to influence properties) provide unique and versatile features from these matrices. The compressive strengths of gas foamed and salt leached porous silk matrices are comparable with various materials used in tissue engineering to make scaffolds as well as with the strength of cortical bone and cartilage. We discovered that salt leached silk scaffolds exhibited the best mechanical properties including that they had a high compressive modulus as well as compressive stress, and they were not brittle. However, the porous silk fibroin material of the present invention is not limited to this method of production.

In a preferred embodiment, scaffold features include high porosity, interconnected pores, biocompatibility, degradability, and pore sizes large enough for cell growth (greater than or equal to about 50-100 µm).

The methods useful for silk scaffold fabrication according to the present invention include (a) gas foaming, and (b) solvent casting/particulate leaching (Freyman et al. *Progress in Materials Science* 2001; 46:273-282; Mikos et al. *Electronic Journal of Biotechnology, Accurate,* 2000; 3:No. 2; Thomson et al. *Biomaterials,* 1998; 19:1935-1943; Widmer et al. *Biomaterials,* 1998; 19:1945-1955; Zhang R.& Ma P. *Journal of Biomedical Material Science,* 1999; 44:446-455; Nam et al. *Journal of Applied Polymer Science,* Vol. 81, 3008-30021, (2001); Agrawal et al. *Journal of Biomedical Material resources* 2001, 55, 141-150; Harris et al. *Journal of Biomedical Material Research* 1998, 42, 396-402; Hutmacher D. *Journal of biomaterial science polymer science* Edn 2001. 12, 107-124). The preferred method for material fabrication is leaching.

In the preferred embodiment, the solvent casting/particulate leaching method involves mixing a water-soluble porogen, for example, NaCl with a viscous silk polymer solution (Freyman et al. *Progress in Materials Science* 2001; 46:273-282; mikos et al. *Electronic Journal of Biotechnology, Accurate,* 2000; 3:No. 2; Agrawal et al. *Journal of Biomedical Material resources* 2001, 55, 141-150; Hutmacher D. *Biomaterials* 2000. 21, 2529-2543; Hutmacher D. *Journal of biomaterial science polymer science Edn* 2001. 12, 107-124). The mixture is cast into a Teflon container where the solvent is evaporated. The result is a salt/polymer composite. The composite is immersed in water to leach out the salt, resulting in a porous three-dimensional structure.

The silk proteins suitable for use in the present invention is preferably fibroin or related proteins (i.e., silks from spiders). As used herein, the term "fibroin" includes selected proteins such as silk from spiders. Preferably, fibroin is obtained from a solution containing a dissolved silkworm silk or spider silk. The silkworm silk protein is obtained, for example, from *Bombyx mori,* and the spider silk is obtained from *Nephila clavipes.* In the alternative, the silk proteins suitable for use in the present invention can be obtained from a solution containing a genetically engineered silk, such as from bacteria, yeast, mammalian cells, transgenic animals or transgenic plants.

Silk polymer or silk fibroin solution according to the present invention can be prepared by any conventional method known to one skilled in the art. For example, *B. mori* cocoons are boiled for about 30 minutes in an aqueous solution. Preferably, the aqueous solution is about 0.02M $Na_2CO_3$. The cocoons are rinsed, for example with water, to extract the sericin proteins and the extracted silk is dissolved in an aqueous salt solution. Salts useful according to the present invention include, lithium bromide, lithium thiocyanate, calcium nitrate or other chemical capable of solubilizing silk. Preferably, the extracted silk is dissolved in about 9-12 M LiBr solution. The salt is consequently removed using, for example, dialysis. See FIG. 1A.

The silk polymer solution is formed by mixing about 5% to 35% by weight of the silk fibroin with a solvent. Preferably about 17% (w/v) of silk is used. Solvents useful according to the present invention include hexa-fluoro-iso-propanyl (HFIP), N-methyl morpholine N-oxide and calcium nitrate-methanol. The preferred solvent is HFIP.

The silk polymer/solvent solution of the present invention is placed into a form, or mold, containing water-soluble particles, or porogens, that are insoluble in organic solvents. Alternatively, the porogens are mixed with the silk polymer solution prior to placement in the mold. The diameter of the particles are preferably between about 50-1000 microns. Examples of water-soluble porogens useful according to the present invention include, NaCl, alkali metals, alkali earth metal halides, phosphates, and sulfates, sugar crystals, water-soluble microspheres, polysaccharides and protein microspheres.

The solvent is consequently removed using, for example, sublimation or evaporation. The polymer solution is treated with an effective amount of alcohol to induce β-sheet structure and insolubility in aqueous solution.

The composite or polymer is immersed in water or other solvent in which the particles, or porogens are soluble and polymer is insoluble, to remove the particles, resulting in a porous three-dimensional structure, referred herein to as a "silk fibroin scaffold" or "silk fibroin material." See FIG. 1B.

In general, regenerated silk fibroin is soluble in water and requires immersion in an alcohol or other suitable agent to obtain the β-sheet structure so that it will be insoluble (Sofia et al. *Journal of Biomedical materials research* 2001, 54, 139-148). Therefore, prior to submersion into aqueous solutions the silk scaffolds are first soaked in a β-sheet structure inducing agent, such as alcohol to induce the phase transition to β-sheet structure. The type of a β-sheet structure inducing agent can be used to generate scaffolds with different properties. For example, as shown in the following examples, when methanol and propanol are used to induce β-sheet structure, the resulting scaffolds are stronger but more brittle and therefore suitable in bone regeneration.

Figure 16A:
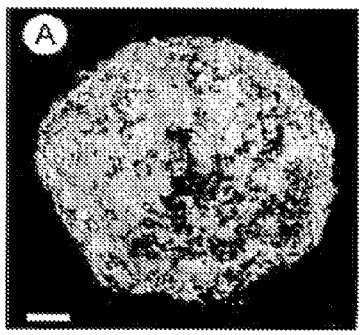
FIGS. 16A-L show µ-CT images of tissue engineered bone on three silk scaffolds with mean pore sizes of 106 µm (16A, 16D, 16G), 225 µm (16B, 16E, 16H), and 425 µm (16C, 16F, 16I). The first row (16A-16C) shows a face view, the second row (16D-16F) a lateral view and the third row (16G-16I) a magnification of A-C. 16J-16L shows scaffolds prior to tissue culture of a mean pore size of 106 µm, 225 µm, and 425 µm respectively.
Figure 16B:
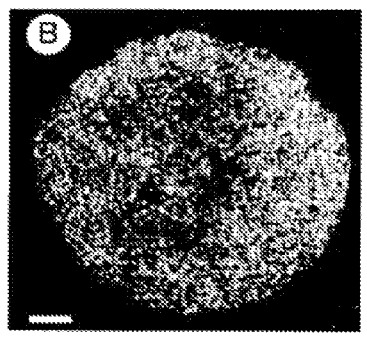
Figure 16C:
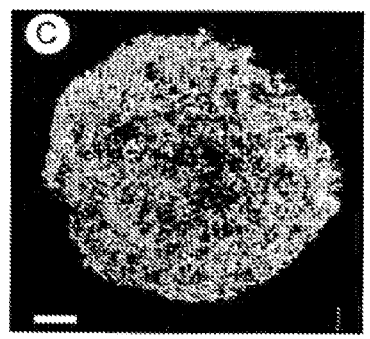
Figure 16D:
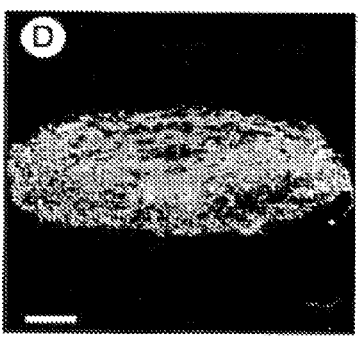
Figure 16E:
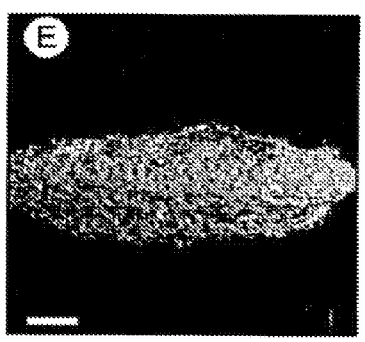
Figure 16F:
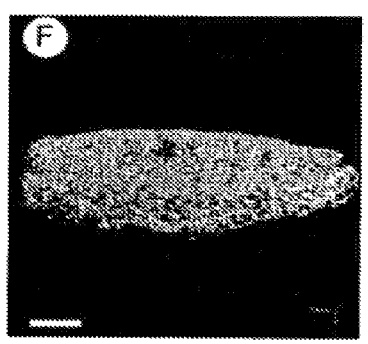
Figure 16G:
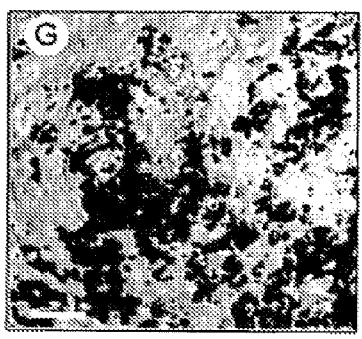
Figure 16H:
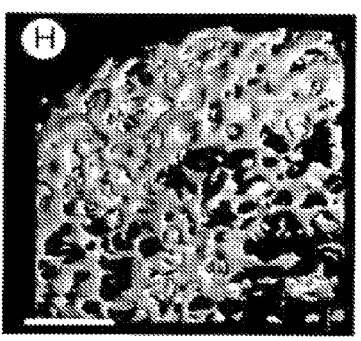
Figure 16I:
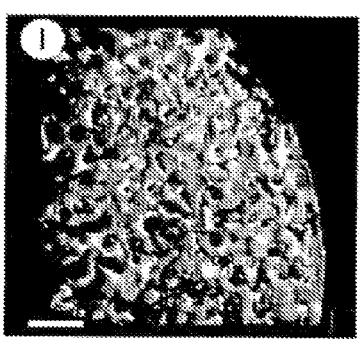
Figure 16J:
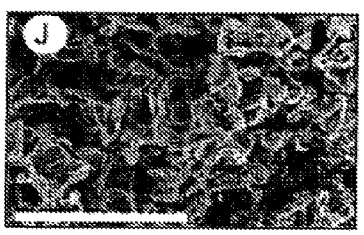
Figure 16K:
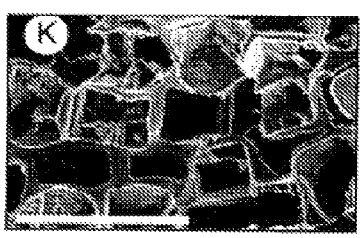
Figure 16L:
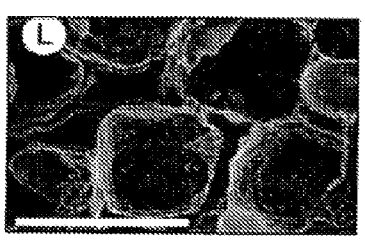

The present invention provides porous silk materials that can be used as scaffolds in tissue regeneration. The porous silk of the present invention have strong mechanical properties as well as pore structure and interconnections among the pores, as shown in FIG. 16J-16L. The density and porosity of the silk scaffolds can be measured by liquid displacement, similar to published methods (Zhang et al. *Journal of Biomedical Material Science,* 1999; 44:446-455). Preferred liquids for use in liquid displacement measurements include those that do not cause shrinkage or swelling of the silk, such as Hexane.

The density of the silk fibroin material is expressed as:

$$d = W/(V_2 - V_3);$$

where
   d=density
   W=weight
   $V_1$=Volume liquid in a container
   $V_2$=total volume of fibroin material and liquid after placement of material in the container
   $V_3$=residual liquid after removal of fibroin material from the container.

The porosity of the silk fibroin material ($\epsilon$) is measured by the following formula:

$$\epsilon = (V_1 - V_3)/(V_2 - V_3).$$

The scaffold material of the present invention is relatively easy to fabricate and has a controlled porous architecture to allow for cell in-growth and tissue regeneration. The ability to adjust porosity provides a means by which an organized three-dimensional tissue with a shape and cellular organization substantially similar to that of the tissue in vivo can be produced.

The porous silk scaffolds of the present invention may further include additives. The additives can be covalently coupled to the scaffold by means known to those skilled in the art. Alternatively, the additive can be added to media surrounding the scaffold.

Additives suitable for use with the present invention includes biologically or pharmaceutically active compounds. Examples of biologically active compounds include, but are not limited to: cell attachment mediators, such as collagen, elastin, fibronectin, vitronectin, laminin, proteoglycans, or peptides containing known integrin binding domains e.g. "RGD" integrin binding sequence, or variations thereof, that are known to affect cellular attachment (Schaffner P & Dard 2003 *Cell Mol Life Sci*. January; 60(1):119-32; Hersel U. et al. 2003 *Biomaterials*. November; 24(24):4385-415); biologically active ligands; and substances that enhance or exclude particular varieties of cellular or tissue ingrowth. For example, the steps of cellular repopulation of the scaffold matrix preferably are conducted in the presence of growth factors effective to promote proliferation of the cultured cells employed to repopulate the matrix. Agents that promote proliferation will be dependent on the cell type employed. For example, when fibroblast cells are employed, a growth factor for use herein may be fibroblast growth factor (FGF), most preferably basic fibroblast growth factor (bFGF) (Human Recombinant bFGF, UPSTATE Biotechnology, Inc.). Other examples of additive agents that enhance proliferation or differentiation include, but are not limited to, osteoinductive substances, such as bone morphogenic proteins (BMP); cytokines, growth factors such as epidermal growth factor (EGF), platelet-derived growth factor (PDGF), insulin-like growth factor (IGF-I and II) TGF-$\beta$, and the like. As used herein, the term additive also encompasses antibodies, DNA, RNA, modified RNA/protein composites, glycogens or other sugars, and alcohols.

The scaffolds can be shaped into articles for tissue engineering and tissue guided regeneration applications, including reconstructive surgery. The structure of the scaffold allows generous cellular ingrowth, eliminating the need for cellular preseeding. The porous polymer scaffolds may also be molded to form external scaffolding for the support of in vitro culturing of cells for the creation of external support organs.

The silk fibroin scaffolds of the present invention may also be mixed with other biocompatible polymers to form mixed polymer scaffolds. Two or more biocompatible polymers can be added to the aqueous solution together with the silk polymer. The biocompatible polymer preferred for use in the present invention is selected from the group comprising polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid and other biocompatible polymers.

The scaffold functions to mimic the extracellular matrices (ECM) of the body. The scaffold serves as both a physical support and an adhesive substrate for isolated cells during in vitro culture and subsequent implantation. As the transplanted cell populations grow and the cells function normally, they begin to secrete their own ECM support.

In the reconstruction of structural tissues like cartilage and bone, tissue shape is integral to function, requiring the molding of the scaffold into articles of varying thickness and shape. Any crevices, apertures or refinements desired in the three-dimensional structure can be created by removing portions of the matrix with scissors, a scalpel, a laser beam or any other cutting instrument. Scaffold applications include the regeneration of tissues such as nervous, musculoskeletal, cartilaginous, tendenous, hepatic, pancreatic, ocular, integumentary, arteriovenous, urinary or any other tissue forming solid or hollow organs.

The scaffold may also be used in transplantation as a matrix for dissociated cells such to create a three-dimensional tissue or organ. Tissues or organs can be produced by methods of the present invention for any species.

A number of different cell types or combinations thereof may be employed in the present invention, depending upon the intended function of the tissue engineered construct being produced. These cell types include, but are not limited to: smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells. For example, smooth muscle cells and endothelial cells may be employed for muscular, tubular constructs, e.g., constructs intended as vascular, esophageal, intestinal, rectal, or ureteral constructs; chondrocytes may be employed in cartilaginous constructs; cardiac muscle cells may be employed in heart constructs; hepatocytes and bile duct cells may be employed in liver constructs; epithelial, endothelial, fibroblast, and nerve cells may be employed in constructs intended to function as replacements or enhancements for any of the wide variety of tissue types that contain these cells. In general, any cells may be employed that are found in the natural tissue to which the construct is intended to correspond. In addition, progenitor cells, such as myoblasts or stem cells, may be employed to produce their corresponding differentiated cell types. In some instances it may be preferred to use neonatal cells or tumor cells.

Cells can be obtained from donors (allogenic) or from recipients (autologous). Cells can also be of established cell culture lines, or even cells that have undergone genetic engineering. Pieces of tissue can also be used, which may provide a number of different cell types in the same structure.

Appropriate growth conditions for mammalian cells are well known in the art (Freshney, R. I. (2000) Culture of Animal Cells, a Manual of Basic Technique. Hoboken N.J., John Wiley & Sons; Lanza et al. Principles of Tissue Engineering, Academic Press; 2nd edition May 15, 2000; and Lanza & Atala, Methods of Tissue Engineering Academic Press; 1st edition October 2001). Cell culture media generally include essential nutrients and, optionally, additional elements such as growth factors, salts, minerals, vitamins, etc., that may be selected according to the cell type(s) being cultured. Particular ingredients may be selected to enhance cell growth, differentiation, secretion of specific proteins, etc. In general, standard growth media include Dulbecco's Modified Eagle Medium, low glucose (DMEM), with 110 mg/L pyruvate and glutamine, supplemented with 10-20% fetal bovine serum (FBS) or calf serum and 100 U/ml penicillin are appropriate as are various other standard media well known to those in the art. Growth conditions will vary dependent on the type of mammalian cells in use and tissue desired.

In one embodiment, methods are provided for producing bone or cartilage tissue in vitro comprising culturing multipotent cells on a porous silk fibroin scaffold under conditions appropriate for inducing bone or cartilage formation. Suitable conditions for the generation of bone and cartilage are well known to those skilled in the art. For example, conditions for the growth of cartilage tissue often comprise nonessential amino acids, ascorbic acid-2-phosphate, dexamethasone, insulin, and TGF-β1. In one preferred embodiment, the nonessential amino acids are present at a concentration of 0.1 mM, ascorbic acid-2-phosphate is present at a concentration of 50 ug/ml, dexamethasone is present at a concentration of 10 nM, insulin is present at a concentration of 5 ug/ml and TGF-β1 is present at a concentration of 5 ng/ml. Suitable conditions for the growth of bone often include ascorbic acid-2-phosphate, dexamethasone, β-glycerolphoasphate and BMP-2. In a preferred embodiment, ascorbic acid-2-phosphate is present at a concentration of 50 ug/ml, dexamethasone is present at a concentration of 10 nM, β-glycerolphoasphate is present at a concentration of 7 mM and BMP-2 is present at a concentration of 1 ug/ml.

In general, the length of the growth period will depend on the particular tissue engineered construct being produced. The growth period can be continued until the construct has attained desired properties, e.g., until the construct has reached a particular thickness, size, strength, composition of proteinaceous components, and/or a particular cell density. Methods for assessing these parameters are known to those skilled in the art.

Following a first growth period the construct can be seeded with a second population of cells, which may comprise cells of the same type as used in the first seeding or cells of a different type. The construct can then be maintained for a second growth period which may be different in length from the first growth period and may employ different growth conditions. Multiple rounds of cell seeding with intervening growth periods may be employed.

In one preferred embodiment, tissues and organs are generated for humans. In other embodiments, tissues and organs are generated for animals such as, dogs, cats, horses, monkeys, or any other mammal.

The cells are obtained from any suitable donor, either human or animal, or from the subject into which they are to be implanted. As used herein, the term "host" or "subject" includes mammalian species, including, but not limited to, humans, monkeys, dogs, cows, horses, pigs, sheep, goats, cats, mice, rabbits, rats.

The cells that are used for methods of the present invention should be derived from a source that is compatible with the intended recipient. The cells are dissociated using standard techniques and seeded onto and into the scaffold. In vitro culturing optionally may be performed prior to implantation. Alternatively, the scaffold is implanted into the subject, allowed to vascularize, then cells are injected into the scaffold. Methods and reagents for culturing cells in vitro and implantation of a tissue scaffold are known to those skilled in the art.

Cells can be seeded within the matrix either pre- or post matrix formation, depending on the method of matrix formation. Uniform seeding is preferable. In theory, the number of cells seeded does not limit the final tissue produced, however optimal seeding may increase the rate of generation. The number of seeded cells can be optimized using dynamic seeding (Vunjak-Novakovic et al. *Biotechnology Progress* 1998; Radisic et al. *Biotechnoloy and Bioengineering* 2003).

It is another aspect of the invention that the 3-dimensional porous silk scaffold, described herein, can itself be implanted in vivo and serve as tissue substitute (e.g. to substitute for bone or cartilage). Such implants, would require no seeding of cells, but contain an addition e.g., RGD, that attracts cells.

In one embodiment, silk matrix scaffolds are seeded with multipotent cells in the presence of media that induces either bone or cartilage formation. Suitable media for the production of cartilage and bone are well known to those skilled in the art.

As used herein, "multipotent" cells have the ability to differentiate into more than one cell type in response to distinct differentiation signals. Examples of multipotent cells include, but are not limited to, bone marrow stromal cells (BMSC) and adult or embryonic stem cells. In a preferred embodiment BMSCs are used. BMSCs are multipotential cells of the bone marrow which can proliferate in an undifferentiated state and with the appropriate extrinsic signals, differentiate into cells of mesenchymal lineage, such as cartilage, bone, or fat (Friedenstein, A. J. 1976. *Int Rev Cytol* 47:327-359; Friedenstein et al. 1987. *Cell Tissue Kinet* 20:263-272; Caplan, A. I. 1994. *Clin Plast Surg* 21:429-435; Mackay et al. 1998. *Tissue Eng* 4:415-428; Herzog et al. *Blood.* 2003 Nov. 15; 102(10):3483-93. Epub 2003 Jul. 31).

The formation of cartilaginous tissue or bone can be monitored by assays well known to those in the art including, but not limited to, histology, immunohistochemistry, and confocal or scanning electron microscopy (Holy et al., *J. Biomed. Mater. Res* (2003) 65A:447-453).

Using silk based scaffolds, organized tissue with a predetermined form and structure can be produced either in vitro or in vivo. For example, tissue that is produced ex vivo is functional from the start and can be used as an in vivo implant. Alternatively, the silk based structure can be seeded with cells capable of forming either bone or cartilage and then implanted as to promote growth in vivo. Thus, the scaffolds can be designed to form tissue with a "customized fit" that is specifically designed for implantation in a particular patient. For example, cartilaginous tissue or bone tissue produced by methods of the present invention can be used to replace large cartilage or bone defects found in musculoskeletal disorders and degenerative diseases such as osteoarthritis or rheumatism. Engineered bone and cartilage are also suitable for spine and joint replacements such as, elbow, knee, hip or finger joints or can be used in osteochondral implants.

EXAMPLES

Example I

Preparation of Scaffolds

Three fabrication techniques; freeze-drying, salt leaching and gas foaming, were used to form porous three-dimensional silk biomaterial matrices. Matrices were characterized for morphological and functional properties related to processing method and conditions. The porosity of the salt leached scaffolds varied between 84-98% with a compressive strength up to 175±3 KPa and the gas foamed scaffolds had porosities of 87-97% and compressive strength up to 280±4 KPa. The freeze-dried scaffolds were prepared at different freezing temperatures (−80 and −20° C.), and subsequently treated with different concentrations (15 and 25%) and hydrophilicity alcohols. The porosity of these scaffolds was up to 99% and the maximum compressive strength was 30±2 KPa. Changes in silk fibroin structure during processing to form the 3D matrices was determined by FT-IR and XrD. The salt leached and gas foaming techniques produced scaffolds with a useful combination of high compressive strength, interconnected pores and pore sizes greater than 100 microns in diameter.

1. Materials

Cocoons of *B. mori* silkworm silk were kindly supplied by M Tsukada, Institute of Sericulture, Tsukuba, Japan and Marion Goldsmith, University of Rhode Island, USA. Sodium chloride and ammonium bicarbonate granules were purchased from Sigma. Hexa-fluoro-iso-propanol (HFIP), methanol, 2-propanol, and 1-butanol, were purchased from Aldrich and used without further purification.

Preparation of Regenerated *B. mori* Silk Fibroin Solutions

*B. mori* silk fibroin was prepared as follows as a modification of our earlier procedure (Nam & Young, *Science* 2001, 81, 3008-30021). Cocoons were boiled for 30 min in an aqueous solution of 0.02 M $Na_2CO_3$ then rinsed thoroughly with water to extract the glue-like sericin proteins. The degummed silk was then dissolved in 9-12 M LiBr solution at room temperature yielding a 7-8% (w/v) solution. This solution was dialyzed in water using Slide-a-Lyzer dialysis cassettes (Pierce, MWCO 2000). The final concentration of the aqueous silk fibroin solution was about 2-5.8 wt %, which was determined by weighing the remaining solid after drying. The HFIP silk solutions were prepared by dissolving the silk fibroin produced after lyophilizing the aqueous silk solution into the HFIP.

3D Scaffold Fabrication by Gas Foaming or Salt Leaching Using Silk Solution in HFIP A viscous silk solution was prepared by dissolving 17% (w/v) silk in HFIP (FIG. 1). Ammonium bicarbonate or sodium chloride particulates (salts particle sizes were 150 to 250 µm) acting as porogens were added to Teflon disk-shaped molds (diameter and height: 18 and 23 mm). The silk/HFIP solution was added into the Teflon molds containing the porogen. The molds were covered to reduce evaporation rate to provide sufficient time for more homogenous distribution of the solution in the mold. The weight ratios of porogen to silk were adjusted to 10:1 and 20:1, respectively. The solvent in the mixture of silk/porogen was evaporated at room temperature. Just before exposure to water, the composite of silk/porogen was immersed in alcohol (methanol, 1-butanol or 2-propanol) for 30 minutes to induce β-sheet structure and insolubility in aqueous solution. The scaffolds with the ammonium bicarbonate were immersed in 95° C. water to induce gas foaming for approximately 10 min until no bubbles were visible and then placed into cold water for an additional 24 hours. The composites that used salt as a porogen were placed into cold water for 24 hours to insure that all the salt had leached from the matrices to avoid negative impact on cells in future studies. The water was changed four times a day. The porous silk scaffolds were air dried and then placed in a vacuum dryer for 24 hr.

Scaffold Fabrication by Freeze-Drying Using Aqueous Silk Solutions

A viscous silk precipitate in gel paste form was prepared by adding 15 or 25 vol % of methanol or propanol to an aqueous silk solution (5.8 wt %) with gentle mixing (FIG. 1). In this phase of the study 1-butanol was not used as a solvent because of its immiscibility in water. A gel paste mixture of the silk/alcohol/water was put into the Teflon disk-shaped molds. The solution was frozen in dry ice for 2 hour and then placed in a container, which controlled the freezing rate at −1° C./min. The containers were placed into either a −20° C. or −80° C. freezer for 2 hrs. The ice/alcohol/silk composite was then lyophilized leaving a porous matrix. In the freeze-drying method, methanol, which is poor solvent for the silk and induces the formation of β-sheet structure, was used to induce crystallization and insolubility in water. The alcohol concentrations were varied between 15 and 25%, selected based on prior studies.

Scaffold Characterization

SEM

The surface and cross-section morphologies of the scaffolds and pore distributions, sizes, and interconnectivity were observed with a LEO Gemini 982 Field Emission Gun SEM. Segments of the outer surface and inner area of the scaffold were prepared by fracture of scaffolds in liquid nitrogen. The specimens were sputter coated with gold. The pore sizes were determined by measuring random samples of ten pores from the SEM images using Corel computer software.

Density and Porosity

The density and porosity of the silk scaffolds were measured by liquid displacement, similar to the published methods (Zhang et al. *Journal of Biomedical Material Science*, 1999; 44:446-455).

Hexane was used as the displacement liquid since it is a non-solvent for silk and is able to easily permeate through the scaffold and not cause swelling or shrinkage, unlike ethanol. A sample of weight W was immersed in known volume (V1) of hexane in a graduated cylinder. The sample was left in the hexane covered for approximately 5 min. In this time the contents in the cylinder underwent an evacuation-repressurization cycle to force the hexane through the pores. The total volume of the hexane and the hexane-impregnated scaffold was V2. The volume difference (V2−V1) is the volume of the polymer scaffold. The hexane-impregnated scaffold was then removed from the cylinder and the residual hexane volume was recorded as V3. The quantity (V1−V3)—volume of hexane within the scaffold—was determined as the void volume of the scaffold. The total volume of the scaffold: $V=(V_2-V_1)+(V_1-V_3)$. The density of the foam is expressed as:

$$d=W/(V_2-V_3)$$

and the porosity of the foam (s) was obtained by:

$$\epsilon=(V_1-V_3)/(V_2-V_3)$$

Mechanical Properties

The compression modulus of the scaffolds was evaluated at room temperature on an Instron 881 equipped with a 100N load cell. Cross-head speed was set at 2 mm/min. Cylinder-shaped samples measuring 8.7 mm in diameter and ranging between 3.2 and 9.5 mm in height were used, according to a modification based on ASTM method F451-95. The compressive stress and strain were graphed and the average compressive strength as well as the compressive modulus and standard deviation determined. The elastic modulus is the ratio of the stress to strain when deformation is totally elastic; also a measure of stiffness, and the compressive strength is the maximum engineering stress that may be sustained without (Callister et al., 2000 In Materials Science Engineering; An Introduction; John Wiley & Sons, Inc, New York, pp 114-127).

FTIR

The infrared spectra of the silk fibroin structures were measured with a FT-IR (Bruker Equinox 55) spectrophotometer. The samples were cast on a ZnS cell crystal surface directly from silk fibroin solution. The cast films were treated with alcohols directly. Each spectrum for samples was acquired in transmittance mode by accumulation of 256 scans with a resolution of 4 $cm^{-1}$ and a spectral range of 4000-400 $cm^{-1}$. The crystallization effect was investigated on the foams by alcohol type; methanol and 2-propanol. X-ray diffraction was used to determine crystal structure in the scaffolds from the freeze-drying method. Wide angle X-ray diffraction (WAXD) experiments were conducted on a Bruker D8 Discover X-ray diffractometer with general area detector diffraction (GADDS) multiwire area detector; 40 KV, 20 mA and 0.5 mm collimator. The distance between the detector and the sample for WAXD was 81.4 mm (CuKα).

Summary of Results and Discussion

Porous silk matrices were formed using three processing methods: freeze-drying, gas foaming, and salt leaching. FIG. 2 shows SEM images of freeze-dried scaffolds processed with 15% methanol or 15% 2-propanol, at −20° C. or −80° C. The scaffolds formed highly interconnected and porous structures. The general size of pores observed were small, with diameters of 50±20 μm. Some of the scaffolds formed two layers, an upper more porous flake-like layer and a bottom layer that was more condensed and compact that was less brittle. At high concentrations of alcohol (>25%) the silk 3D scaffolds were brittle. The higher the concentration of silk fibroin in solution the smaller the pores.

Silk fibroin in solution or frozen at low temperature is generally in a random coil structure based on FTIR analysis. Some aggregation occurs during this process. The silk porous matrices formed at −80° C. resulted in similar morphologies, regardless of the freezing rate or alcohol type and concentration used in the processing. Pores were small, ~10 microns in diameter, and very fine silk aggregates were observed. There was a difference in morphology when comparing the forms formed with methanol versus 2-propanol at −20° C. With 2-propanol a more leaf or sheet like morphology was observed; while with the methanol smaller spherical pores were formed. The methanol formed foams were friable and easily broken, unlike the scaffolds formed from 2-propanol. These results likely reflect differences in miscibility of the two alcohols with water, since 2-propanol is not highly miscible, leading to larger pore features.

The glass transition temperature is important in the formation of pores within the silk fibroin matrix. The glass transition zone of silk in an aqueous solution is, −20 to −34° C. (Li, M. et al. *Journal of Applied Polymer Science* 2001, 79, 2185-2191; Nam, J et al. *Journal of Applied Polymer Science* 2001, 81, 3008-30021). The higher the freezing temperature above the glass transition the longer it will take for ice to form and grow. Therefore, the ice particles will have a greater effect on the size of the pores. The longer the freezing time then the larger the pores. Once the temperature is below the glass transition zone, the pore size is no longer dependent on the temperature. FIG. 2 shows that as the temperature was decreased to −80° C. the pore diameters decreased to 15±7 μm (Table 1) and the silk fibroin formed small aggregates. As the freezing temperature increased the pore diameter increased based on SEM. The size of ice particles is dependent on their growth rate and time (Li, M. et al. *Journal of Applied Polymer Science* 2001, 79, 2185-2191; Nam, J et al. *Journal of Applied Polymer Science* 2001, 81, 3008-30021; Ishaug-Riley et al. *Biomaterials* 1998, 19, 1405-1412). Above the glass transition the solution is in a stable region where there is slow growth of ice crystals resulting in a macroporous structure (Li, M. et al. *Journal of Applied Polymer Science* 2001, 79, 2185-2191; Li, M et al. *Journal of Applied Polymer Science* 2001, 79, 2192-2199; Nam, J et al. *Journal of Applied Polymer Science* 2001, 81, 3008-30021). Below the glass transition zone quick freezing shortens the growing time of the ice crystals making it more difficult to grow large ice particles, therefore resulting in an unstable region where microporous interconnected structures are formed (Nam, J et al. *Journal of Applied Polymer Science* 2001, 81, 3008-30021; Ishaug-Riley et al. *Biomaterials* 1998, 19, 1405-1412).

The porogen particles used for the salt leaching and gas foaming techniques were not sieved to obtain a specific porogen size. Therefore, the resulting pores followed a Gaussian distribution. The salt leached scaffolds (FIGS. 3 and 4) used NaCl as a porogen, which were leached out in water to form the porous matrix. These scaffolds formed pore sizes 202±112 μm. The scaffolds varied in structure, some were more ductile, while others were more brittle. The pores were larger in comparison to those generated by the freeze-drying method. However, the pore structure was not as highly interconnected; both open and closed pore structures were observed. A skin layer formed on the surface of the salt leached scaffolds, which decreased with an increase in porosity.

Scaffolds formed by gas foaming were processed using ammonium bicarbonate as the porogen. The gas foamed scaffolds with higher porosity were not as strong and flaked apart. SEM images showed a highly interconnected open pore morphology with diameters in the range of 155±114 μm. The gas foamed process did not leave a skin layer on the surface of the scaffold. Larger pores could also be formed if larger salt particles were used, the process is only limited by the size of the porogen selected.

Porosity

Matrices with up to 99% porosity were formed depending on the processing method: freeze-drying, gas foaming, and salt leaching (Table 1). The scaffolds prepared by freeze-drying resulted in porosities ~99%, regardless of the variables studied. With salt leaching and gas foaming, and varying the porogen, (salt to silk ratio of 10:1 or 20:1, wt/wt) the porosities were 84±1% to 98±4% for the salt leached scaffolds and 87±2% to 97±3% for the gas foamed scaffolds.

TABLE 1

Porosity and density of the scaffolds (Ave ± S.D., N = 3) for porosity and density measures. For pore sizes, N = 200.

| Methods | Sample | ε(%)[1] | d[2] | Pore size (μm) |
|---|---|---|---|---|
| Gas Foaming | $NH_4HCO_3$/Silk (wt %) | | | |
| | 10:1 | 87.0 ± 2.0 | 100 ± 10 | 155 ± 114 |
| | 20:1 | 97.0 ± 1.0 | 40 ± 5 | |
| Salt Leaching | NaCl/Silk (wt %) | | | |
| | 10:1 | 84.0 ± 2.0 | 120 ± 2 | 202 ± 112 |
| | 20:1 | 98.0 ± 1.0 | 40 ± 13 | |
| Freeze Drying | Alcohol treatment[3] | | | |
| (Frozen at −20° C.) | 15% Methanol | 98.0 ± 0.10 | 20 ± 2 | 50 ± 20 |
| | 25% Methanol | 99.0 ± 0.01 | 30 ± 1 | |
| | 15% Propanol | 98.0 ± 0.01 | 30 ± 3 | |
| | 25% Propanol | 99.0 ± 0.20 | 30 ± 3 | |
| (Frozen at −80° C.) | 15% Methanol | 99.0 ± 0.30 | 50 ± 3 | 15 ± 7 |
| | 15% Propanol | 99.0 ± 0.03 | 40 ± 1 | |
| | 15% Propanol | 97.0 ± 0.20 | 30 ± 3 | |
| | 25% Propanol | 99.0 ± 0.02 | 30 ± 5 | |

[1]Porosity
[2]Density (mg/ml)
[3]Weight ratio of water in alcohol

Structure

Figure 5:
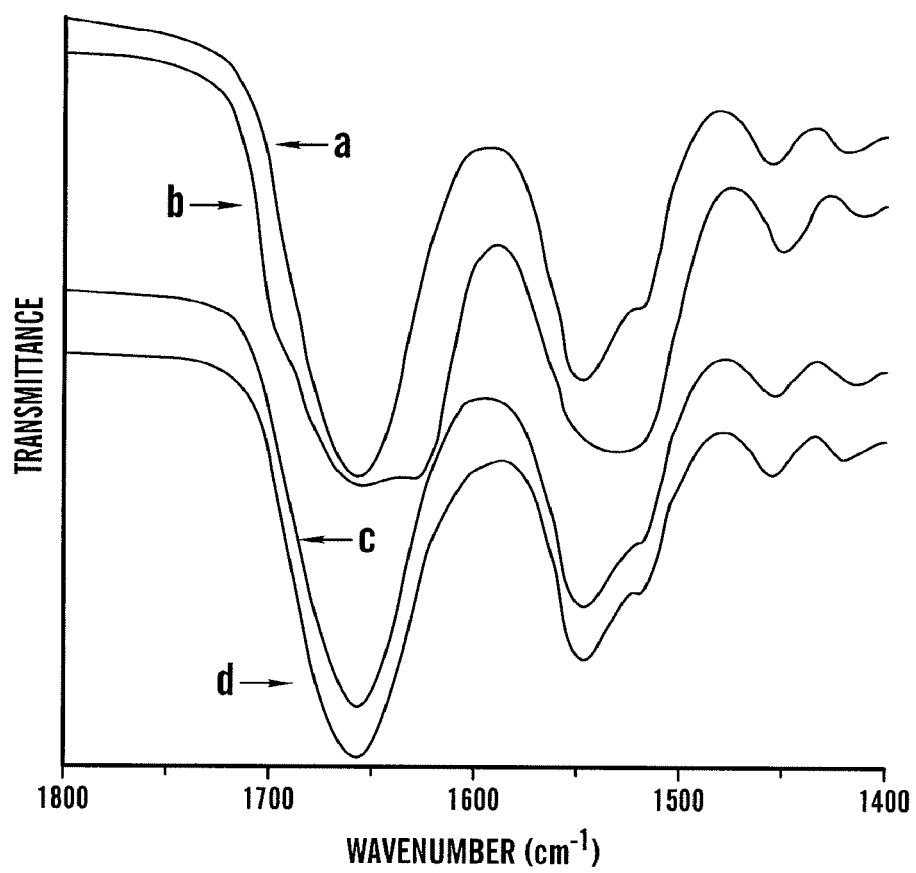
FIG. 5 shows FTIR of silk fibroin before immersion in alcohol (curve a, silk I), after immersion in methanol (curve b, silk II), 1-butanol (curve c, silk I) and 2-propanol (curve d, silk I).
Figure 6B:
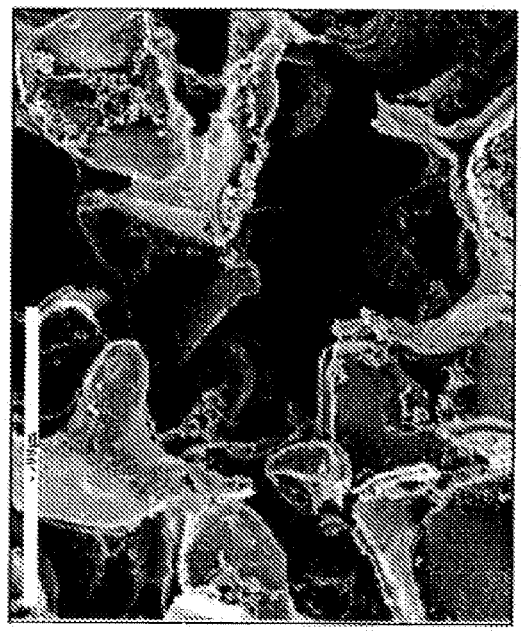
FIGS. 6A and 6B show scanning electron microscopy of collagen (6A) and silk (6B) scaffolds. Bar length=500 µm.
Figure 6A:
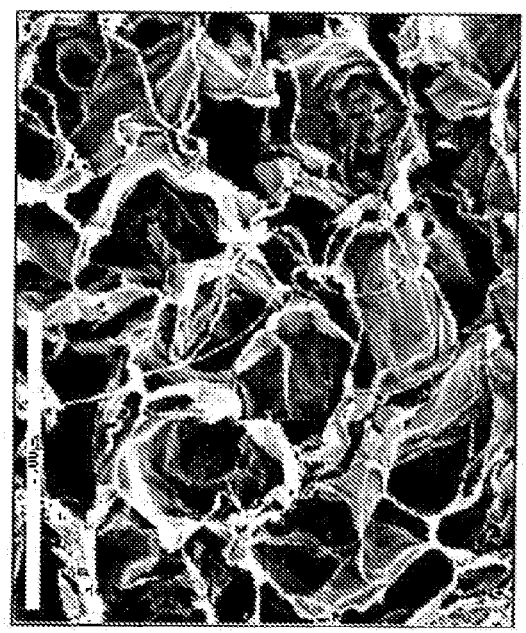

FTIR spectra of silk fibroins immersed in methanol, 2-propanol, and 1-butanol were observed (FIG. 5). β-sheet structure was observed for samples immersed in methanol with peaks at 1627.7 and 1524.8 $cm^{-1}$. Silk I peaks are at 1658.5 and 1524.8 $cm^{-1}$. Samples immersed in 2-propanol showed no shift from silk I to β-sheet structure. The samples immersed in 1-butanol showed a slight shift in the peak at 1700 $cm^{-1}$, indicating slight β-sheet conformation. X-ray diffraction spectra of freeze-dried silk scaffolds were analyzed to determine crystallization effects of alcohol and temperature on the silks scaffolds. The diffraction peaks indicated β-sheet structure for the freeze-dried scaffolds frozen at −80° C. using 25% methanol (FIG. 6). The scaffolds treated with iso-propanol and frozen at −20° C. with 15% methanol had no β-sheet structure, corroborating the FTIR interpretations.

Mechanical Properties

The structure of the freeze-dried scaffolds was foam like and very porous. The compressive strength (Table 2) of 15% and 25% methanol treated foams formed at −20° C. were 10±2 and 10±3 KPa, respectively, with a compressive modulus of 20±1 and 10±3 KPa, respectively. The foams processed using 15 and 25% 2-propanol had a compressive strength of 10±2 and 10±3 KPa, respectively, and a compressive modulus of 40±4 and 50±8 KPa, respectively. The structures of the foams treated with propanol were more compact and less porous macroscopically, they did not flake apart easily. The foams processed using methanol were flakier and easily broken.

Methanol is a hydrophilic alcohol, miscible with water, and when it comes into contact with a silk solution it induces the chains of fibroin to interact with each other (Li, M. et al. *Journal of Applied Polymer Science* 2001, 79, 2185-2191; Li, M et al. *Journal of Applied Polymer Science* 2001, 79, 2192-2199; Nam, J et al. *Journal of Applied Polymer Science* 2001, 81, 3008-30021; Magoshi, J. *Kobunshi Ronbunshu* 1974, 31, 765-770; Magoshi, J. et al. *Applied Polymer Symposia* 1985, 41, 187-204). The fibroin silk chains are then able to organize into a β-sheet structure. When silk is in the β-sheet structure it is in a crystalline form making it more brittle. 2-Propanol is less hydrophilic than methanol and therefore less miscible with water. When added to the silk fibroin solution there is a phase separation. Since propanol is not as miscible as methanol, less water is drawn from the silk and less β-sheet structure forms when compared to the methanol treated foams (Li, M. et al. *Journal of Applied Polymer Science* 2001, 79, 2185-2191; Li, M et al. *Journal of Applied Polymer Science* 2001, 79, 2192-2199; Nam, J et al. *Journal of Applied Polymer Science* 2001, 81, 3008-30021; Magoshi, J. *Kobunshi Ronbunshu* 1974, 31, 765-770; Magoshi, J. et al. *Applied Polymer Symposia* 1985, 41, 187-204). The foams containing 2-propanol are not crystalline and are tougher, therefore with a higher compressive modulus than those processed with methanol. With an increase in the concentration of methanol there is an increase in compressive modulus. This decrease occurs because of the increase in crystallinity. With a higher concentration of methanol, more rapid and extensive chain rearrangements occur leading to a higher content of β-sheets within the foam (Li, M. et al. *Journal of Applied Polymer Science* 2001, 79, 2185-2191; Li, M et al. *Journal of Applied Polymer Science* 2001, 79, 2192-2199).

With the scaffolds prepared at −80° C. with alcohol, methanol and 2-propanol, at concentrations of 15 and 25%, there is an increase in the compressive strength and compressive modulus (Table 2).

TABLE 2

Compressive stress and modulus of the silk scaffolds.

| Method | Sample | Alcohol Treatment[1] | Compressive stress (kPa) | Compressive Modulus (kPa) |
|---|---|---|---|---|
| Gas Foaming | $NH_4HCO_3$/Silk (wt %) | | | |
| | 10:1 | Methanol | 280 ± 4 | 900 ± 94 |
| | | 1-Butanol | 230 ± 9 | 500 ± 37 |
| | | 2-Propanol | 250 ± 28 | 800 ± 44 |
| | 20:1 | Methanol | 250 ± 21 | 1000 ± 75 |
| | | 1-Butanol | 150 ± 8 | 300 ± 40 |
| | | 2-Propanol | 100 ± 11 | 200 ± 30 |
| Salt Leaching | NaCl/Silk (wt %) | | | |
| | 10:1 | Methanol | 30 ± 10 | 100 ± 2 |
| | | 1-Butanol | 150 ± 14 | 400 ± 50 |
| | | 2-Propanol | 100 ± 20 | 400 ± 58 |
| | 20:1 | Methanol | 175 ± 3 | 450 ± 94 |
| | | 1-Butanol | 250 ± 4 | 490 ± 94 |
| | | 2-Propanol | 200 ± 3 | 790 ± 3 |
| Freeze Drying | Freeze Temperature | | | |
| | −20° C. | none | 80 ± 1 | 170 ± 7 |
| | | 15% Methanol | 10 ± 2 | 20 ± 1 |
| | | 25% Methanol | 10 ± 3 | 10 ± 3 |
| | | 15% 2-Propanol | 10 ± 2 | 40 ± 4 |
| | | 25% 2-Propanol | 10 ± 3 | 50 ± 8 |
| | −80° C. | none | 20 ± 2 | 220 ± 7 |
| | | 15% Methanol | 20 ± 3 | 90 ± 21 |
| | | 25% 2-Propanol | 5 ± 4 | 90 ± 40 |
| | | 15% Methanol | 30 ± 2 | 100 ± 1 |
| | | 25% 2-Propanol | 20 ± 1 | 130 ± 1 |

[1]100% unless otherwise indicated, weight percent of the alcohol in water.

This increase may be due to the increased freezing rate induced by the temperature decrease. At this point the foams are able to form only small pores, even though the foams are highly porous, and the compressive force may distributed differently within this structure of the foams.

The gas foamed scaffolds were also treated with alcohols before compressive mechanical test. Scaffolds immersed in methanol and propanol had higher compressive strengths and compressive modulus; 280±4 KPa and 900±94 KPa, respectively, and 250±28 and 800±44 KPa, respectively. When mechanically crushed, the scaffolds flaked apart and were not as ductile as those produced by the salt leached method. There was a dramatic difference in compressive stress between the scaffolds with 87% porosity versus 97% porosity. Scaffolds with a high porosity had a lower compressive strength than the low porosity foams (Table 2).

The salt leached scaffolds prepared using a 10:1 salt to silk ratio had compressive strengths from 30 and 150 KPa depending on alcohol treatment (Table 2). Values were higher for the 20:1 samples. These scaffolds were immersed in methanol, 1-butanol, and 2-propanol. The scaffolds with 84% porosity were thin and formed thick skin layers, therefore data were not reliable due to the heterogeneous structure.

The gas foamed scaffolds generated a definite compressive yield point where the scaffold was no longer able to maintain its original features. However, the salt leached scaffolds showed characteristics that were more ductile and sponge-like in behavior. After maximum compression was reached densification occurred and the scaffold was crushed yet did not flake apart. The cells of the scaffold no longer maintained their shape.

The salt leached scaffolds varied in ductility. The pore structure of the salt leached scaffolds was not uniform perhaps due to the evaporation of the organic solvent, HFIP, and the increase in the polymer concentration of the remaining solution entrapped within the salt bed. The outer surface of the salt leached scaffolds formed a dense skin layer; common when highly volatile solvents are evaporated from the interior region of a matrix (Nam, Y. S. et al. *Biomaterials* 1999, 20, 1783-1790). The evaporation of the organic solvent from the surface forced the formation of a thick film on the scaffold allowing very few pores to form for the rest of the solvent to evaporate. This residual solvent in the matrix function as a plasticizer and makes the polymer more ductile. It often takes up to three days to remove the residual solvent from these silk matrices, due to this dense skin layer, based on weight changes over time.

The gas foamed scaffolds had a higher compressive strength and compressive modulus than the salt leached scaffolds. The reasons for this difference in mechanical properties may be the uniform distribution of the pores within the gas foamed scaffolds which lead to more consistent mechanical properties, and/or the pore sizes themselves. The stress applied to the matrix is concentrated at pore interfaces and if the pore distribution is not uniform then the polymer matrix can typically deform at a lower compressive strength (Harris, L. D et al. *Journal of Biomedical Material Research* 1998, 42, 396-402; Ehrenstein, G. W. Mechanical Behavior. In Polymeric Materials; Structure, Properties, and Applications; Hanser/Gardener Publications, Inc., Cincinnati, 2001; pp 167-182). Since the salt leached scaffold consists of both open and closed pore structures the distribution of the compressive forces was uneven, causing the scaffold to collapse at lower stress (Harris, L. D. et al. *J. Journal of Biomedical Material Research* 1998, 42, 396-402).

The mechanical data show the deformation and compression trends of the scaffolds as load is applied. In tissue engineering scaffolds for bone-related applications, matrices are usually designed to hold a load that will allow for 1 to 2% strain (Table 3). The gas foamed scaffolds and the salt leached scaffolds treated with methanol were analyzed. Of the scaffolds prepared and evaluated these are the most likely to be used in bone tissue regeneration, therefore the secant modulus, used to assess stress-strain relationships at a specific load level (Kim, S.; Cho, et al. *Fibers and Polymers* 2001, 2, 64-70), were determined. Compared to porous biodegradable polymeric scaffolds often considered in bone-related tissue engineering studies, the silk porous scaffolds had similar properties at 1 and 2% strain. The gas foamed scaffolds showed the highest compressive modulus. These data are also comparable to the strength of cortical bone and cartilage (Table 4).

TABLE 3

Average compressive strength and average compressive modulus of gas foamed and salt leached scaffold at 1% and 2% strain under compressive load. (N = 2)

| Scaffold | Porogen ratio | Average compressive modulus (KPa) at 1% strain | Average compressive strength (KPa) at 1% strain | Average compressive modulus (KPa) at 2% strain | Average compressive strength (KPa) at 2% strain |
|---|---|---|---|---|---|
| Salt Leached | 10:1 | 40 | 0.40 | 400 | 8 |
|  | 20:1 | 1600 | 16 | 1200 | 24 |
| Gas Foamed | 10:1 | 500 | 5 | 200 | 16 |
|  | 20:1 | 5000 | 50 | 3000 | 60 |

TABLE 4

Mechanical properties of three-dimensional porous scaffolds using polymeric material, and cortical bone (Suh, H. Yonsei *Medical Journal* 1998, 39, 87-96).

| MATERIAL | Compression Modulus (KPa) | Compressive strength (KPa) |
|---|---|---|
| cortical bone | 15-30 (GPa) | — |
| PLGA[a] | 159 ± 130 | — |
| PLGA[b] | 289 ± 25 | — |
| PLLA[c] | 242 ± 32 | — |
| PLLA[d] | 65 ± 5 | — |
| collagen[e] | ~150 | ~15 |
| chitosan[f] | ~750 | ~45 |
| collagen/chitosan[g] | ~500 | ~30 |
| silk fibroin | 3,000 | 50 |

[a] poly (d,L-lactic-co-glycolic acid) and NaCl particles were compression molded to form PLGA/NaCl composite. 95% porous scaffold processed using salt leaching method (Harris, L. D.; Kim, B.-S.; Mooney, D. J. Journal of Biomedical Material Research 1998, 42, 396-402).
[b] poly (D,L-lactic-co-glycolic acid) 95% porous scaffold processed using gas foaming method(Harris, L. D.; Kim, B.-S.; Mooney, D. J. Journal of Biomedical Material Research 1998, 42, 396-402).
[c] poly(L-lactic acid) designed using gas foaming method and $NH_4HCO_3$ particles as porogen. The weight ratio of $NH_4HCO_3$ to PLLA is 10:1 (Nam, Y. S.; Yoon, J. J.; Park, T. G. J. Biomed. Mater. Res. 2000, 53, 1-7).
[d] poly(L-lactic acid) designed using gas foaming method and $NH_4HCO_3$ particles as porogen. The weight ratio of $NH_4HCO_3$ to PLLA is 20:1(Nam, Y. S.; Yoon, J. J.; Park, T. G. J. Biomed. Mater. Res. 2000, 53, 1-7)..
[e] porous collagen sponge processed by lyophilization (Kim, S et al. Fibers and Polymers 2001, 2, 64-70).
[f] Porous chitosan sponge processed by lyophilization (Kim, S et al. Fibers and Polymers 2001, 2, 64-70).
[g] porous sponge made of crosslinked collagen/chitosan, processed by lyophilization (Kim, S et al. Fibers and Polymers 2001, 2, 64-70).

Example II

Engineering of 3-Dimensional Cartilage Tissue

Materials

Bovine serum, RPMI 1640 medium, Dulbecco's Modified Eagle Medium medium, basic fibroblast growth factor (bFGF), transforming growth factor-β1 (TGF-β1), Pen-Strep, Fungizone, non essential amino acids, trypsin were from Gibco (Carlsbad, Calif.). Ascorbic acid phosphate, Histopaque-1077, insulin, and dexamethasone were from Sigma (St. Lois, Mo.). Collagen scaffolds (Ultrafoam) were from Davol (Cranston, R.I.). All other substances were of analytical or pharmaceutical grade and obtained from Sigma. Silkworm cocoons were kindly supplied by M. Tsukada, Institute of Sericulture, Tsukuba, Japan, and Marion Goldsmith, University of Rhode Island).

Scaffold Preparation and Decoration

Cocoons from *Bombyx Mori* were boiled for 1 hour in an aqueous solution of 0.02M Na2CO3, and rinsed with water to extract sericins. Purified silk was solubilized in 9M LiBr solution and dialyzed (Pierce, MWCO 2000 g/mol) against PBS for 1 day and again against 0.1M MES, 0.5 M NaCl, pH 6 buffer for another day. An aliquot of the silk solution was coupled with GRGDS peptide to obtain RGD-silk. For coupling COOH groups on the silk were activated by reaction with 1-ethyl-3-(dimethylaminopropyl)carbodiimide hydrochloride (EDC)/N-hydroxysuccinimide (NHS) solution for 15 minutes at room temperature (Sofia et al. 2001. *J Biomed Mater Res* 54:139-148). To quench the EDC, 70 µl/ml β-mercaptoethanol was added. Then 0.5 g/l peptide was added and left for 2 hours at room temperature. The reaction was stopped with 10 mM hydroxylamine. Silk solutions were dialyzed against 0.1 M 2-(N-morpholino)-ethanesulfonic acid buffer, pH 4.5-5 for 1 day. Silk and Silk-RGD solutions were lyophilized and redissolved in hexafluoro-2-propanol (HFIP) to obtain a 17% (w/v) solution. Granular NaCl was weighed in a Teflon container and silk/HFIP solution was added at a ratio of 20:1 (NaCl/silk). HFIP was allowed to evaporate for 2 days and NaCl/silk blocks were immersed in 90% (v/v) methanol for 30 minutes to induce a protein conformational transition to β-sheet (Nazarov et al. 2003. In *Department of Biomedical Engineering*. Medford: Tufts University). Blocks were removed, dried and NaCl was extracted in water for 2 days. Disk shaped scaffolds (5 mm diameter, 2 mm thick) were prepared using a dermal punch (Miltey, Lake Success, N.Y.), and autoclaved.

For cross-linking, collagen scaffolds were incubated in 0.1M MES, 0.5 M NaCl, pH=6 buffer for 30 min and subsequently crosslinked with 1.713 g EDC and 0.415 g NHS in 100 ml 0.1M MES, 0.5 M NaCl, pH=6 buffer per gram of collagen (van Wachem et al. 2001. *J Biomed Mater Res* 55:368-378). The reaction was allowed to proceed for 4 hrs under gentle shaking and was stopped by washing for 2 hrs with 0.1 M Na2HPO4. The films were rinsed 4 times for 30 min with water. The whole procedure was carried out aseptically.

Human Bone Marrow Stromal Cell Isolation and Expansion.

Total bone marrow (25 cm$^3$, Clonetics, Santa Rosa, Calif.) was diluted in 100 ml of isolation medium (5% FBS in RPMI 1640 medium). Cells were separated by density gradient centrifugation. Briefly, 20 ml aliquots of bone marrow suspension were overlaid onto a poly-sucrose gradient ($\delta$=1,077 g/cm$^3$, Histopaque, Sigma, St. Louis, Mo.) and centrifuged at 800×g for 30 min at room temperature. The cell layer was carefully removed, washed in 10 ml isolation medium, pelleted and contaminating red blood cells were lysed in 5 ml of Pure-Gene Lysis solution. Cells were pelleted and suspended in expansion medium (DMEM, 10% FBS, 1 ng/ml bFGF) and seeded in 75 cm$^2$ flasks at a density of 5×10$^4$ cells/cm$^2$. The adherent cells were allowed to reach approximately 80% confluence (12-17 days for the first passage). Cells were trypsinized, replated and passage 2 (P2) cells (80% confluence after 6-8 days), were used for the experiments.

Tissue Culture

Passage 2 mesenchymal stem cells (7×10$^5$ cells) were suspended in 40 μl DMEM and the suspension was used to seed scaffolds, which were prewetted overnight in DMEM. Seeded constructs were placed in 6-well Petri dishes and incubated at 37° C. for 2 hours to allow cell attachment. To maintain moisture 30 μl DMEM was added to the scaffolds every 30 minutes. Subsequently, 5 ml of chondrogenic or control medium was added per well. Control medium was DMEM, supplemented with 10% fetal bovine serum and Pen-Strep. Chondrogenic medium included the control medium was further supplemented with 0.1 mM nonessential amino acids, 50 μg/ml ascorbic acid-2-phosphate, 10 nm dexamethasone, 5 μg/ml insulin, 5 ng/ml TGF-β1. Medium was exchanged every 2-3 days and constructs were harvested after 2 and 4 weeks.

Biochemical Analysis and Histology

Constructs were cultured for 6 hours (0 weeks), 1, 2, and 4 weeks in control or chondrogenic medium and processed for biochemical analysis and histology. For DNA analysis, 3-4 constructs per group and time point were disintegrated after 6 hours (0 weeks), 1, 2 and 4 weeks in culture using steel balls and a Microbeater. DNA content (n=3-4) was measured using the PicoGreen assay (Molecular Probes, Eugene, Oreg.), according to the protocol of the manufacturer. Samples were measured fluorometrically at an excitation wavelength of 480 nm and an emission wavelength of 528 nm. For the MTT assay 3-4 constructs were transferred to 2 ml plastic tubes, and 1.5 ml serum free DMEM was added to each well supplemented with MTT (0.5 g/l) and incubated in the dark at 37° C., 5% CO2 for 2 hours. Tubes were centrifuged for 10 minutes at 2000 g and the supernatant was aspirated. Isopropyl alcohol (1.5 ml) was added and constructs were disintegrated using steel balls and a Microbeater. Tubes were centrifuged at 2000 g for 10 minutes and absorption was measured at 570 nm. Sulphated glycosaminoglycan (GAG) deposition (n=5), was assessed as previously described (Martin et al. 1999. *Ann Biomed Eng* 27:656-662). Briefly, constructs were frozen, lyophilized for 3 days, weighed, and digested for 16 hours at 60° C. with proteinase-K. GAG content was determined colorimetrically by dimethylmethylene blue dye binding and measured spectrophotometrically at 525 nm (Farndale et al. 1986. *Biochim Biophys Acta* 883:173-177).

RNA Isolation, Real-Time-Reverse Transcription Polymerase Chain Reaction (Real Time RT-PCR)

Fresh constructs (n=3-4 per group) were transferred into 2 ml plastic tubes and 1.5 ml Trizol was added. Constructs were disintegrated using steel balls and a Microbeater. Tubes were centrifuged at 12000 g for 10 minutes and the supernatant was transferred to a new tube. Chloroform (200 μl) was added to the solution and incubated for 5 minutes at room temperature. Tubes were again centrifuged at 12000 g for 15 minutes and the upper aqueous phase was transferred to a new tube. One volume of 70% ethanol (v/v) was added and applied to an RNeasy mini spin column (Quiagen, Hilden, Germany). The RNA was washed and eluted according to the manufacturer's protocol. The RNA samples were reverse transcribed in cDNA using oligo (dT)-selection according to the manufacturer's protocol (Superscript Preamplification System, Life Technologies, Gaithersburg, Md.). Collagen type 2, MMP1, and MMP2 gene expression was quantified using the ABI Prism 7000 Real Time PCR system (Applied Biosystems, Foster City, Calif.). PCR reaction conditions were 2 min at 50° C., 10 min at 95° C., and then 50 cycles at 95° C. for 15 s, and 1 min at 60° C. The expression data were normalized to the expression of the housekeeping gene, glyceraldehyde-3-phosphate-dehydrogenase (GAPDH). Probes were labeled at the 5' end with fluorescent dye FAM (VIC for GAPDH) and with the quencher dye TAMRA at the 3' end. Primer sequences for the human collagen type 2 gene were: Forward primer 5'-GGC AAT AGC AGG TTC ACG TAC A-3' (SEQ ID NO:1), reverse primer 5'-CGA TAA CAG TCT TGC CCC ACT T-3' (SEQ ID NO:2), probe 5'-CCG GTA TGT TTC GTG CAG CCA TCC T-3' (SEQ ID NO:3). Primer sequences for the human GAPDH gene were: Forward primer 5'-ATG GGG AAG GTG AAG GTC G-3' (SEQ ID NO:4), reverse primer 5'-TAA AAG CCC TGG TGA CC-3' (SEQ ID NO:5), probe 5'-CGC CCA ATA CGA CCA AAT CCG TTG AC-3' (SEQ ID NO:6). Primers and probes for MMP1 and MMP2 were purchased from Applied Biosciences (Assay on Demand # Hs00233958 ml (MMP1), Hs 00234422 ml (MMP2))

Histology, Immunohistochemistry and Scanning Electron Microscopy

For histology, constructs were dehydrated, embedded in paraffin and cut in 5 μm sections were. To stain for cartilage tissue, sections were treated with eosin for 1 min, fast green for 5 min, and 0.2% aqueous safranin O solution for 5 min, rinsed with distilled water, dehydrated through xylene, mounted, and placed under a coverslip (Rosenberg, L. 1971. *J Bone Joint Surg Am* 53:69-82).

For immunohistochemistry using a monoclonal antibody against type 2 collagen (2B1.5, dilution 1:100, Neomarkers, Fremont, Calif.), paraffin embedded sections of tissue exposed to films were deparraffinized through a series of graded alcohols, treated with protease 2 for 16 min. The primary antibody was added to each slide and incubated for 32 minutes at room temperature in a humidified chamber. The secondary antibody was applied, carrying horseradish peroxidase and developed according to the manufacturer's protocol (BenchMark IHC staining module, Ventana, Tucson, Ariz.). Sections were counterstained using hematoxylin for 2 minutes.

For SEM, constructs were cut and exposed to Karnovsky's fixative (2% paraformaldehye, 2% glutaraldehyde in 0.1M phosphate Buffer). After initial fixation, constructs were again fixed with 1% osmium tetroxide in 0.1M phosphate buffer for 1 hour. After rinsing with PBS for 15 min the constructs were dehydrated using a series of graded ethyl alcohols and dried. Constructs were coated with a thin layer of gold prior to evaluation.

Statistical Analysis

Statistical analysis of data was performed by one-way analysis of variance (ANOVA) and Tukey-Kramer procedure for post hoc comparison. p values less than 0.05 were considered statistically significant.

Results

Proliferation of Human Bone Marrow Stromal Cells on Silk, Silk-RGD, and Collagen Scaffolds The proliferation of BMSCs on silk 3D matrices, silk matrices decorated with the cell adhesion peptide RGD, and collagen control matrices was assessed over 4 weeks (FIG. 6). The scaffolds were of porous character and the lattice was more sheet like for collagen and more sponge like for the silks (FIG. 6).

Figure 7A:
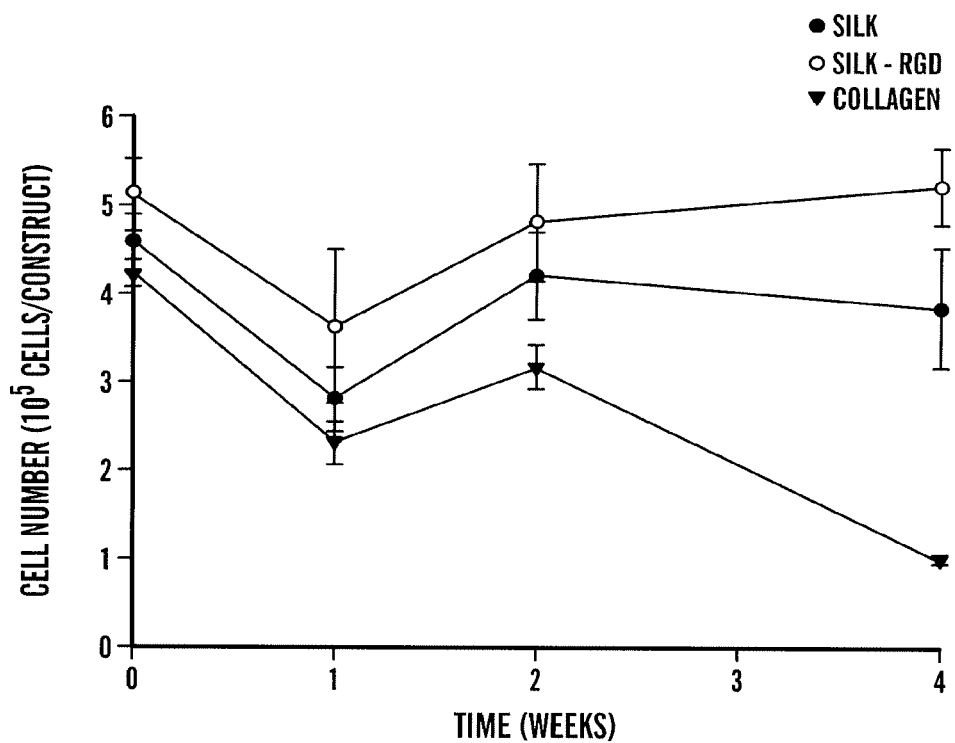
FIGS. 7A and 7B show biochemical characterization of MSC proliferation on silk, silk-RGD, and collagen scaffolds cultured in control medium for 4 weeks in dishes. (7A) DNA content and (7B) MTT activity shown per construct. Data represent the average±standard deviation of 3-4 scaffolds.

A total of $7 \times 10^5$ cells were seeded on each of the matrices, as determined by DNA assay and cell counts. About $4-5 \times 10^5$ cells were found on the matrices 6 hours after seeding (week 0). Cell number dropped approximately 30% for BMSCs cultured on all substrates between week 0 and week 1 (FIG. 7A). After 2 weeks in culture, cell numbers increased and reached initial levels. Cell proliferation was significantly lower on the collagen matrices compared to silk and silk-RGD constructs ($p < 0.05$). After 4 weeks in culture, cell proliferation continued on the silk-RGD scaffolds and was significantly higher than on the silk scaffolds ($p < 0.05$). On the silk scaffolds (with and without RGD), total cell numbers remained stable between weeks 2 and 4 while cell numbers declined on the collagen scaffolds where cell numbers were significantly lower compared to the silk or silk-RGD matrices ($p < 0.001$).

Figure 7B:
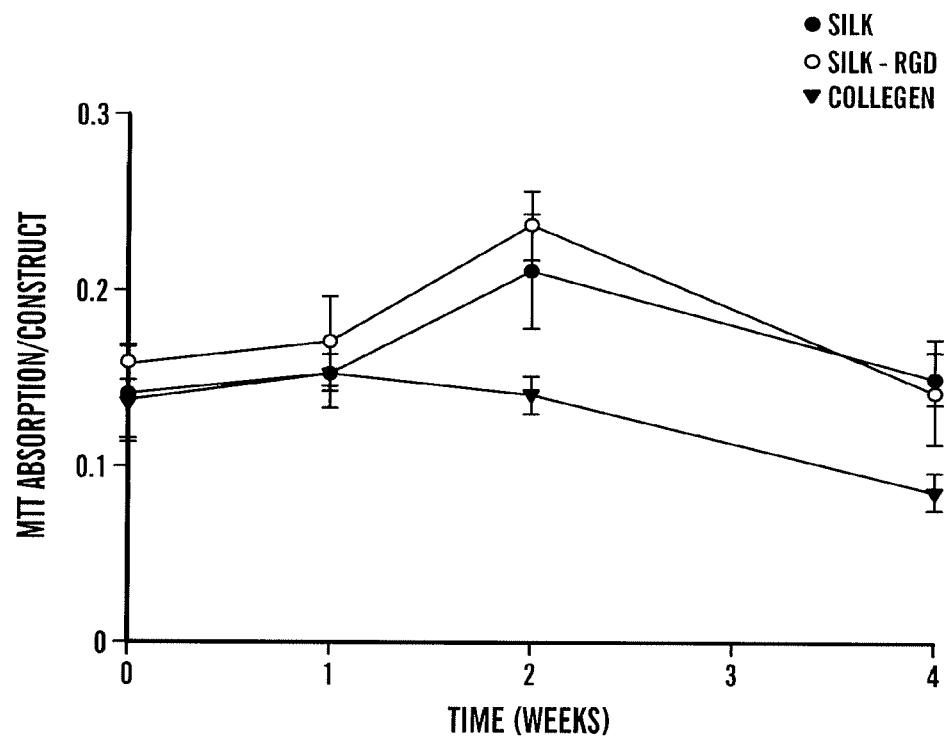

The MTT assay was used to determine cell viability (FIG. 7B). During the first two weeks, cell viability increased on silk and silk-RGD scaffolds, whereas on collagen the numbers were significantly less than on the silk ($p < 0.05$) and the silk-RGD versions ($p < 0.01$) at the 2 week time point. After 4 weeks, cell viability decreased on the silk and silk-RGD matrices and no statistically significant difference was observed for the three biomaterial scaffolds. The loss of cell numbers on collagen scaffolds was accompanied by advanced biodegradation of the biomaterial. Wet weight of matrices seeded with BMSCs and exposed to chondrogenic medium and control medium decreased to 16±6% and 19±6%, respectively, of the initial wet weight. The wet weight of the collagen scaffolds which were not seeded with cells and exposed to control medium for 4 weeks decreased to 25±11% of the initial weight. Cross linked (CL) collagen scaffolds remained stable with a wet weight of 90±5% after 4 weeks in chondrogenic medium. No change in wet weight for silk and silk-RGD matrices was observed in chondrogenic (94±9%) or control media (95±13%), or on the silk scaffolds without cells exposed to control medium (100±3%) during the 4 weeks of culture.

Figure 8A:
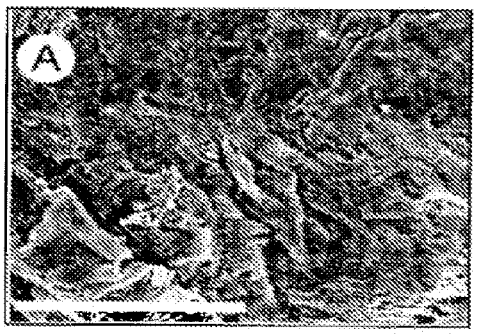
FIGS. 8A-F show scanning electron micrographs of MSCs grown on silk and collagen scaffolds. Face view of collagen (8A) and silk (8B) matrices, cross section of collagen (8C) and silk (8D) matrices cultured in control medium for 4 weeks. Bar=400 µm. (8E, 8F) MSCs cultured for 2 weeks on silk scaffolds. Bar=20 µm (8E), 200 µm (8F).
Figure 8B:
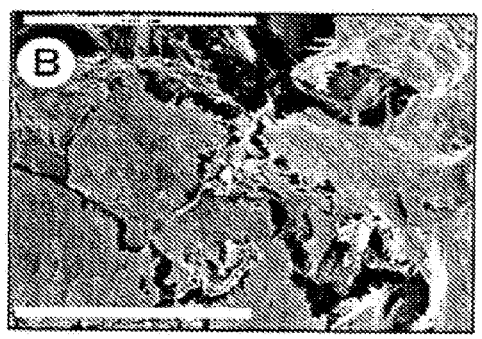

BMSC proliferation resulted in a formation of cell sheets on the surfaces of all scaffolds after 4 weeks in culture (FIG. 8A, 8B). Cross sections of collagen (FIG. 8C) and silk (FIG. 8D) scaffolds demonstrated more homogenous cell growth within the silk matrices compared to collagens. Polymer degradation in the collagen scaffolds resulted in a breakdown of the support lattice structure, whereas the silks retained their structural integrity throughout the experiment.

Figure 8C:
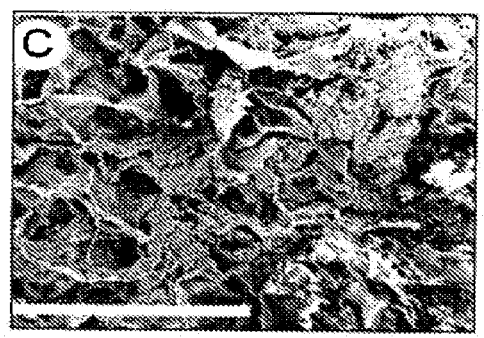
Figure 8D:
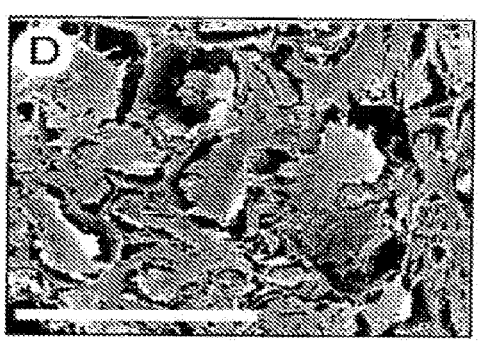
Figure 8E:
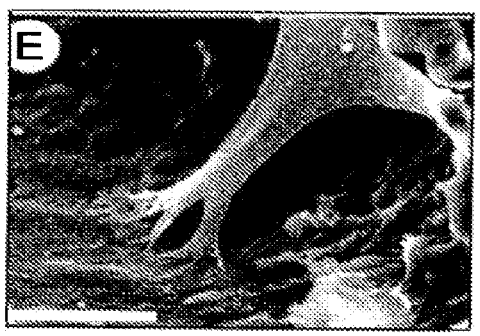
Figure 8F:
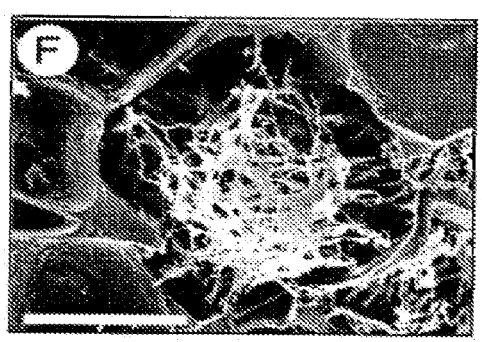

BMSCs attached to the silk scaffolds via cellular extensions (FIG. 8E) and cells formed networks after 2 weeks (FIG. 8F) and sheets after 4 weeks within the silk scaffold pores (FIG. 8D).

Chondrogenesis

Figure 9A:
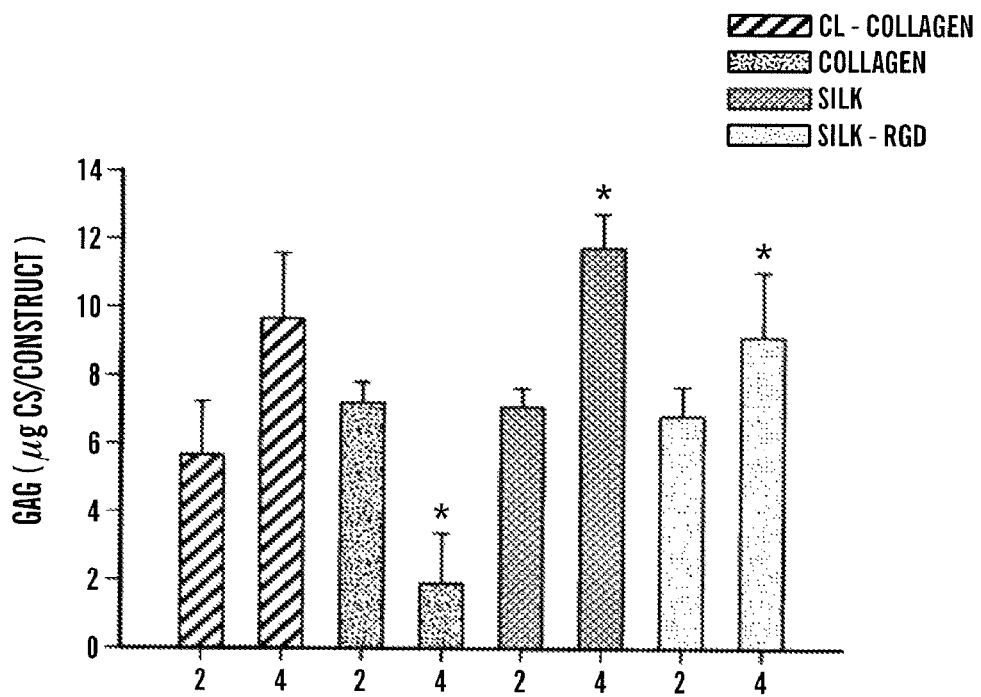
FIGS. 9A and 9B show GAG content expressed as µg chondroitin-sulfate/construct (9A) and chondroitin-sulfate/DNA (g/g) (9B) of MSCs cultured on cross linked-collagen, collagen, silk, and silk-RGD scaffolds after 2 and 4 weeks in chondrogenic medium. One asterisk indicates significant difference to the respective control group ($p<0.05$). Significantly more GAG was detected on the silk matrices compared to collagen when cultured in chondrogenic medium for 4 weeks ($p<0.01$). GAG deposition on the silks was similar to cross-linked collagen.
Figure 9B:
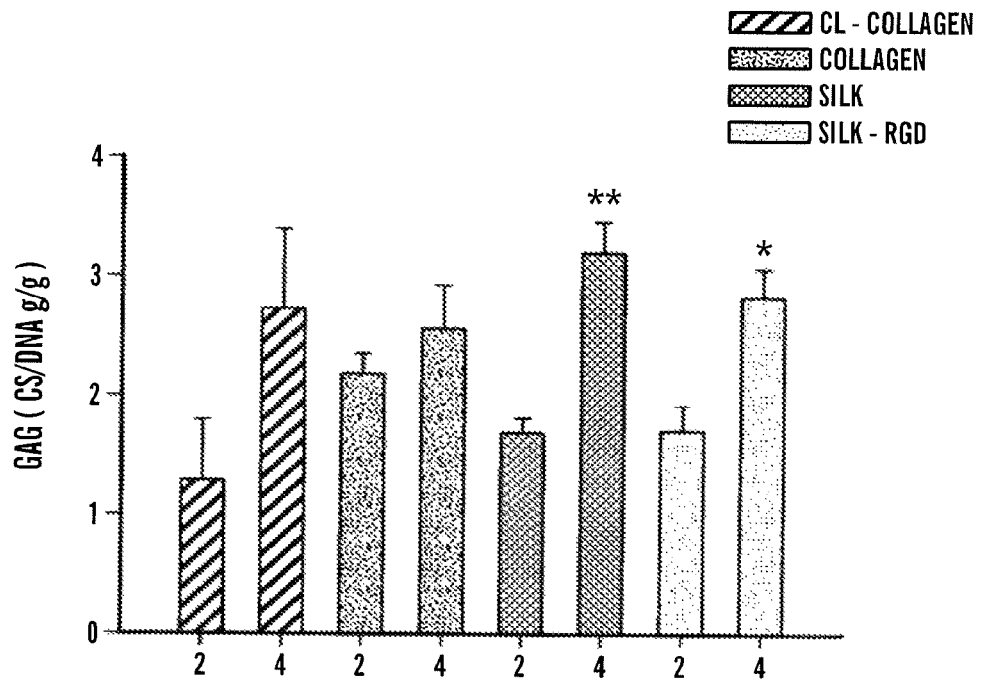

The deposition of sulphated glycosaminoglycans (GAG) on collagen, silk, and silk-RGD matrices after 2 and 4 weeks in culture were assessed (FIG. 9). After 2 weeks GAG deposition was the same on all biomaterials. Total GAG content increased on the silks at 4 weeks ($p < 0.01$ compared to all groups, and $p < 0.001$ compared to collagen) and decreased on collagen after 4 weeks compared to 2 weeks ($p < 0.01$). Upon cross-linking, GAG deposition on the collagen scaffolds was similar and statistically indifferent to the silks.

Expression of interstitial collagenase (MMP1) and gelatinase A (MMP2) on collagen and silk scaffolds cultured in chondrogenic medium were assessed and normalized relative to the expression of the respective constructs cultured in control medium. Neither MMP 1 nor MMP2 expression was significantly increased or decreased in chondrogenic medium as compared to control medium.

Figure 10:
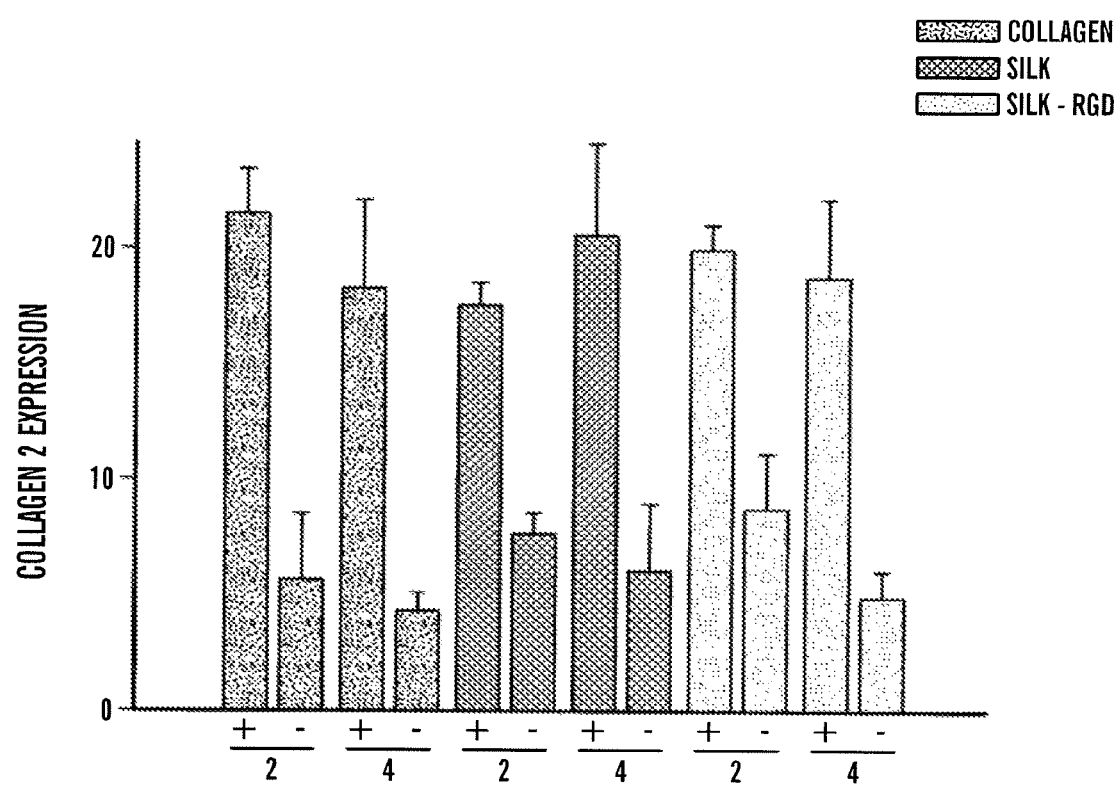
FIG. 10 shows collagen type 2 mRNA expression from cells cultured in chondrogenic medium (+) or control medium (−). Data are normalized to the collagen type 2 expression levels of MSCs at the time of seeding (baseline). Expression was significantly higher for all cells cultured in chondrogenic medium compared to controls ($p<0.01$). Data represent the average±standard deviation of 3-4 constructs.

The hallmark of human cartilage differentiation is the expression of type II collagen. Gene expression of collagen type II by the cells cultured on collagen, silk, and silk-RGD matrices in chondrogenic or control medium was determined after 2 and 4 weeks (FIG. 10). Relative to expression in control medium, over-expression was observed in chondrogenic medium for all biomaterials after 2 and 4 weeks ($p < 0.01$). Compared to the levels measured at the time of seeding (represented by the baseline in FIG. 9), increased expression levels were observed for matrices grown in control medium.

In the presence of chondrogenic medium, round or angular shaped cells resided in cavities or lacunae (FIG. 11). The extracelluar matrix (ECM) was stained with safranin O and the cells were found in the depth of the deposited matrix. ECM-rich areas within collagen constructs were relatively small and 100-200 µm in length. In contrast, 500-700 µm long and interconnected ECM-rich zones were observed within the silk and silk-RGD scaffolds. No differences were observed between the silk and silk-RGD scaffolds. Cells cultured in control medium had spindle-like and fibroblastic morphology and did not stain positive with safranin O. The cartilage-like nature of the deposited matrix was corroborated by immunohistochemistry after 4 weeks. The matrix, which surrounded the round cells stained positive for type 2 collagen on both the collagen and the silks Discussion This work demonstrates that relatively large (500-700 µm) and connected pieces of human cartilage can be generated in vitro by culturing bone marrow stromal cells on highly porous and structurally stable silk scaffolds. This is in contrast to the collagen scaffold used in this study, where degradation was observed and the collapsing matrix prevented a similar outcome. At least two scenarios could account to these observations: (i) the production of matrix metalloproteinases (MMP), leading to enzymatic degradation of the newly deposited cartilage components or (ii) the rapid degradation of the collagen matrix. Diseases such as rheumatoid arthritis, are associated with chondrocytes synthesizing MMPs which collectively degrade all components of cartilage (Cawston et al. 1999. *Ann*

*N Y Acad Sci* 878:120-129). In particular, the collagenolytic enzyme, e.g. interstitial collagenase also known as MMP1, has been strongly implicated in cartilage destruction (Shlopov et al. 1997. *Arthritis Rheum* 40:2065-2074). Our preliminary results suggest that the observed GAG depletion on collagen matrices was not associated with increased MMP1 or MMP2 transcript levels and no over-expression of either enzyme was observed on a RNA level.

The collagen scaffold used in this study was stabilized by physical methods, but its durability could be extended for example by using chemical agents that cross-link the collagen (Carpentier et al. 1969. *J Thorac Cardiovasc Surg* 58:467-483). To understand the significance of biodegradation on the decline in GAG content on collagen scaffolds after 4 versus 2 weeks, cross linked (CL) collagen scaffolds were prepared, in which biodegradation was reduced. GAG content on CL-collagen was similar as compared to the silks after 4 weeks and much higher than on the untreated collagen (FIG. 9). This suggests that the observed loss in GAG content on the natural collagen was mainly due rapid degradation of the scaffold and not to enzymatic effects. Collagen scaffolds prepared by physical processes resemble more the natural collagen and have less cytotoxic effects and better biocompatibility when compared to chemically cross-linked materials (van Luyn et al. 1992. *J Biomed Mater Res* 26:1091-1110). Furthermore, it has been shown that collagen scaffolds prepared by physical processes have less cytotoxic effects and better biocompatibility when compared to chemically cross-linked materials (van Luyn et al. 1992. *J Biomed Mater Res* 26:1091-1110). For purposes of cartilage tissue engineering the use of chemically cross-linked collagen as scaffold material is questionable. In response to implantation of cross-linked collagens, calcification has been observed around the implant (Golomb et al. 1987. *Am J Pathol* 127:122-130). This could potentially interfere with the quality of the tissue engineered cartilage tissue upon implantation. Furthermore silk based materials can cover a broader range of mechanical properties than collagen based materials, which may be a substantial advantage to meet physiological needs at the implantation site (Altman et al. 2003. *Biomaterials* 24:401-416). Because of these constraints and the focus of this study to compare natural polymers, only physically stabilized scaffolds were further characterized and described in this study.

Human BMSCs were cultivated on highly porous silk scaffolds to facilitate cell seeding and medium exchange. Approximately 60% of the administered BMSCs were seeded onto the matrices (FIG. 7A) and cell numbers declined during the first week. Cell viability, as assessed by MTT activity (FIG. 7B), did not decline within this period, suggesting that approximately 80% of the seeded cells, determined by DNA, were alive. This conclusion is also reflected by the loss in cell numbers after 1 week (FIG. 7A). A similar pattern of viability was observed on silk fibres. In accordance to our findings on 3D scaffolds, BMSC viability on silk fibres decreased within the first week by approx. 30% and after 2 weeks in culture the initial viability was retained (Chen et al. 2003. *J Biomed Mater Res* in press). This suggests that the observed pattern in viability is more a function of the biomaterial chemistry and not surface morphology or processing. Seeding strategies can also have a significant impact on the quality of engineered tissues and various static and dynamic seeding strategies have been described to address this issue in three-dimensional scaffolds (Ishaug-Riley et al. 1997. *J Biomed Mater Res* 36:1-8; Carrier et al. 1999. *Biotechnol Bioeng* 64:580-589; Vunjak-Novakovic et al. 1998. *Biotechnol Prog* 14:193-202). Generally, dynamic seeding strategies result in more uniform cell distributions in the scaffolds compared to the static seeding strategy used in the present study. The droplet protocol employed here involved a 2 hour incubation time in the presence of minimal medium to allow cell attachment, likely contributing to the initial loss of cell viability. Cell distribution upon seeding on the collagen was mainly restricted to the outer 200-300 μm of the scaffold surface; cells gradually penetrated the entire scaffold during the incubation period of 4 weeks. These limitations are unlikely to be lessened by using dynamic seeding since the seeding of the center of the collagen scaffold was prevented by physical constraints. In contrast, BMSCs were seeded successfully throughout the silk and silk-RGD scaffolds with almost complete filling of the scaffold voids as seen in histological sections after 1 week (data not shown). The large diameter of interconnected pores together with the stability of the scaffold geometry due to mechanical properties and slow rate of degradation facilitated seeding of the entire constructs. This was also reflected by the homogenous cell distribution on silk scaffolds in contrast to collagen where cells resided in small areas even after 4 weeks in culture (FIG. 8C, 8D). Similarly, large areas of cartilage-like tissue were observed by safranin O staining on silk and silk-RGD scaffolds, whereas this was confined to relatively small areas in the collagen scaffolds (FIG. 11). The cartilage-like nature of the deposited tissue was further confirmed by immunohistochemistry, using antibodies against type 2 collagen and resulting in a strong binding of the antibody (FIG. 11).

After 4 weeks significantly more cells were present on silk and silk-RGD scaffolds than on collagen scaffolds determined by DNA content (FIG. 7A). However, in terms of cell viability no differences could be detected between the biomaterials (FIG. 7B). This can be due to hindrance in diffusion, at least in part created by dense cell sheets covering the surface of the scaffolds after 4 weeks (FIG. 8A, 8B). Dead cells, which are detected by the DNA assay (FIG. 7A) but not by the MTT assay (FIG. 7B), could not leave the scaffold interior due to the occlusion by cell sheets on the surfaces.

Some studies have been performed to study the differentiation of human BMSCs on three-dimensional scaffolds to engineer cartilage has been reported (for a review see (Hunziker, E. B. 2002. *Osteoarthritis Cartilage* 10:432-463). Two of these studies used poly-L-lactic acid (PLA) or poly(lactic-co-glycolic acid) matrices (Caterson et al. 2001. *J Biomed Mater Res* 57:394-403; Martin et al. 2001. *J Biomed Mater Res* 55:229-235). Although these polymers have been widely used in studies with biomaterials, they are known to elicit inflammatory responses mainly due to the release of acidic hydrolysis products (Athanasiou et al. 1996. *Biomaterials* 17:93-102). Recently, we have demonstrated in vitro and in vivo that the inflammatory response elicited by silk, silk-RGD and collagen is lower than due to PLA films (Meinel et al., 2003). GAG deposition/mg scaffold was approximately an order of magnitude less for all biomaterials used in this study than described for PLA scaffolds (Martin et al. 2001. *J Biomed Mater Res* 55:229-235). The study describing chondrogenesis on PLA scaffolds (Martin et al. 2001. *J Biomed Mater Res* 55:229-235) used bovine instead of human BMSCs and twice as much TGF-β1 than used in this study. However deposition of GAG/DNA was similar compared to the PLA study suggesting that the induction of chondrogensis/cell was similar in human and bovine cells. The wet weight for the PLA scaffolds was less than for the silk scaffolds and this could contribute to the higher GAG/mg wet (Martin et al. 2001. *J Biomed Mater Res* 55:229-235).

Stained areas for GAG were larger on silk and silk-RGD scaffolds likely due to the mechanical stability of the silks Decoration of silk scaffolds with RGD adhesion sequences resulted in increased levels of DNA (FIG. 7A), but did not lead to an increase in GAG deposition (FIG. 9), as compared to collagen scaffolds.

This study demonstrates by histological evaluation and biochemical and gene expression analysis that chondrogenesis of bone marrow stromal cells can be induced on both collagen and silk scaffolds. However, the biomechanical properties of collagen were insufficient for cartilage tissue engineering, leading to distributed and unconnected patches within the 3D matrices due to premature degradation and collapse. In contrast, connected cartilage-like tissue was formed in and on silk and silk-RGD matrices. When these results are considered in connection with the unique mechanical properties of silk, the induction of cartilage formation on silk-based materials offers new opportunities for bioengineering of cartilage-like tissue in vitro and the treatment of cartilage defects in vivo.

Example III

Engineering of 3-Dimensional Bone Tissue

Materials

Bovine serum, RPMI 1640 medium, Dulbecco's Modified Eagle Medium (DMEM), basic fibroblast growth factor (bFGF), transforming growth factor-β1 (TGF-β1) (R&D Systems, Minneapolis, Minn.), Pen-Strep, Fungizone, non essential amino acids, trypsin were from Gibco (Carlsbad, Calif.). Ascorbic acid phosphate, Histopaque-1077, insulin, dexamethasone, β-glycerolphosphate were from Sigma (St. Lois, Mo.). Collagen scaffolds (Ultrafoam) were from Davol (Cranston, R.I.). All other substances were of analytical or pharmaceutical grade and obtained from Sigma. Silkworm cocoons were kindly supplied by M. Tsukada (Institute of Sericulture, Tsukuba, Japan) and Marion Goldsmith (University of Rhode Island, Cranston, R.I.).

Scaffold Preparation and Decoration

Cocoons from *Bombyx Mori* (Linne, 1758) were boiled for 1 hour in an aqueous solution of 0.02M Na2CO3, and rinsed with water to extract sericins. Purified silk was solubilized in 9M LiBr solution and dialyzed (Pierce, Woburn, Mass.; MWCO 3500 g/mol) against water for 1 day and again against 0.1M MES (Pierce), 0.5 M NaCl, pH 6 buffer for another day. An aliquot of the silk solution was coupled with glycine-arginine-alanine-aspartate-serine (GRGDS) peptide to obtain RGD-silk. For coupling COOH groups on the silk were activated by reaction with 1-ethyl-3-(dimethylaminopropyl)carbodiimide hydrochloride (EDC)/N-hydroxysuccinimide (NHS) solution for 15 minutes at room temperature (Sofia et al. 2001. *J Biomed Mater Res* 54:139-148). To quench the EDC, 70 µl/ml β-mercaptoethanol was added. Then 0.5 g/l peptide was added and left for 2 hours at room temperature. The reaction was stopped with 10 mM hydroxylamine. Silk solutions were dialyzed against water for 2 days. Silk and Silk-RGD solutions were lyophilized and redissolved in hexafluoro-2-propanol (HFIP) to obtain a 17% (w/v) solution. Granular NaCl was weighed in a Teflon container and silk/HFIP solution was added at a ratio of 20:1 (NaCl/silk). HFIP was allowed to evaporate for 2 days and NaCl/silk blocks were immersed in 90% (v/v) methanol for 30 minutes to induce a protein conformational transition to β-sheets (Nazarov et al. 2003. In *Department of Biomedical Engineering*. Medford: Tufts University). Blocks were removed, dried and NaCl was extracted out in water for 2 days. Disk shaped scaffolds (5 mm diameter, 2 mm thick) were prepared using a dermal punch (Miltey, Lake Success, N.Y.), and autoclaved.

For cross-linking, collagen scaffolds were incubated in 0.1M MES, 0.5 M NaCl, pH=6 buffer for 30 min and subsequently crosslinked with 1.713 g EDC and 0.415 g NHS in 100 ml 0.1M MES, 0.5 M NaCl, pH=6 buffer per gram of collagen (van Wachem et al. 2001. *J Biomed Mater Res* 55:368-378). The reaction was allowed to proceed for 4 hrs under gentle shaking and was stopped by washing for 2 hrs with 0.1 M Na2HPO4. The films were rinsed 4 times for 30 min with water. The whole procedure was carried out aseptically.

Iodiniation of GRYDS Peptide

To assess the amount of bound RGD to the scaffolds, GRYDS peptide was iodinated with non radioactive iodine to quantify the amount of bound peptide in the silk film surface by X-ray photoelectron spectrometer (XPS). The procedure involved first flusing of Sep-Pak C18 reverse phase cartridge (Waters) with 10 ml of a 80:20 mix of methanol:water and then flushing with 10 ml of 0.1M PBS 0.5 NaCl pH=6 buffer, as previously described (Sofia et al. 2001. *J Biomed Mater Res* 54:139-148). Three IODO-BEADS (Pierce) were rinsed once with 1 ml of PBS buffer. Eighty ml of PBS and then 10 µl of 3.75 g/L NaI in PBS were added and the activation was allowed for 5 minutes. Then, 1 ml of 0.1 g/l GRYDS peptide in PBS was added and the reaction was allowed for 15 min. Beads were rinsed with PBS and the peptide solution was injected into the C18 column followed by elution with 0, 20, 40, and 60% methanol in water solutions. Fractions were collected and analyzed at 280 nm. The iodination procedure was repeated with the same peptide through lyophilization of the desired fractions and resolubilizing in buffer to achieve the desired extent of iodination (1 atom of iodine per molecule of GRYDS). Iodinated peptide was coupled to silk matrices as described above for GRGDS.

Human Bone Marrow Stromal Cell Isolation and Expansion

Total bone marrow (25 cm3, Clonetics, Santa Rosa, Calif.) was diluted in 100 ml of isolation medium (5% FBS in RPMI 1640 medium). Cells were separated by density gradient centrifugation. Briefly, 20 ml aliquots of bone marrow suspension were overlaid onto a poly-sucrose gradient ($\delta$=1,077 g/cm3, Histopaque, Sigma, St. Louis, Mo.) and centrifuged at 800×g for 30 min at room temperature. The cell layer was carefully removed, washed in 10 ml isolation medium, pelleted and contaminating red blood cells were lysed in 5 ml of Pure-Gene Lysis solution. Cells were pelleted and suspended in expansion medium (DMEM, 10% FBS, 1 ng/ml bFGF) and seeded in 75 cm2 flasks at a density of $5 \times 10^4$ cells/cm2. The adherent cells were allowed to reach approximately 80% confluence (12-17 days for the first passage). Cells were trypsinized, replated and passage 2 (P2) cells (80% confluence after 6-8 days), were used for the experiments.

Pellet Culture

For pellet culture, $2 \times 10^5$ cells were centrifuged at 300 g for 10 min at 4° C. The medium was aspirated and replaced with osteogenic, chondrogenic, or control medium. Control medium was DMEM supplemented with 10% FBS, Pen-Strep and Fungizone, chondrogenic medium was control medium supplemented with 0.1 mM nonessential amino acids, 50 µg/ml ascorbic acid-2-phosphate, 10 nm dexamethasone, 5 µg/ml insulin, 5 ng/ml TGF β1 and osteogenic medium was control medium supplemented with 50 µg/ml ascorbic acid-2-phosphate, 10 nm dexamethasone, 7 mM β-glycerolphosphate, and 1 µg/ml BMP-2.

Tissue Culture

For cultivation on scaffolds, P2 BMSC ($7 \times 10^5$ cells) were suspended in liquid Matrigel® (10 µl) on ice, and the suspension was seeded onto prewetted (DMEM, overnight) scaffolds. Seeded constructs, placed in dishes were placed in an incubator at 37° C. for 15 minutes to allow gel hardening and osteogenic or control medium was added. Half of the medium was replaced every 2-3 days. Control medium was DMEM supplemented with 10% FBS, Pen-Strep and Fungizone, and osteogenic medium was control medium supplemented with 50 µg/ml ascorbic acid-2-phosphate, 10 nm dexamethasone, 7 mM β-glycerolphosphate, and 1 µg/ml BMP-2.

Biochemical Analysis and Histology

Scaffolds were cultured for 2 and 4 weeks in control or osteogenic medium and processed for biochemical analysis and histology. For DNA analysis, 3-4 scaffolds per group and time point were disintegrated using steel balls and a Microbeater. DNA content (n=3-4) was measured using the PicoGreen assay (Molecular Probes, Eugene, Oreg.), according to the protocol of the manufacturer. Samples were measured fluorometrically at an excitation wavelength of 480 nm and an emission wavelength of 528 nm. Sulphated glycosaminoglycan (GAG) deposition for pellet culture (n=5), was assessed as previously described (Martin et al., 1999 *Ann Biomed Eng* 27:656-662). Briefly, pellets were frozen, lyophilized for 3 days, weighed, and digested for 16 hours at 60° C. with proteinase-K. GAG content was determined colorimetrically by dimethylmethylene blue dye binding and measured spectrophotometrically at 525 nm (Farndale et al. *Biochim Biophys Acta* 883:173-177). For total calcium content, samples (n=4) were extracted twice with 0.5 ml 5% trichloroacetic acid. Calcium content was determined by a colorimetric assay using o-cresolphthalein complexone (Sigma, St. Louis, Mo.). The calcium complex was measured spectrophotometrically at 575 nm. Alkaline phosphatase activity was measured using a biochemical assay from Sigma (St. Louis, Mo.), based on conversion of p-nitrophenyl phosphate to p-nitrophenol which was measured spectrophotometrically at 410 nm.

RNA Isolation, Real-Time-Reverse Transcription Polymerase Chain Reaction (Real Time RT-PCR)

Fresh scaffolds (n=3-4 per group) were transferred into 2 ml plastic tubes and 1.5 ml Trizol was added. Scaffolds were disintegrated using steel balls and a Microbeater. Tubes were centrifuged at 12000 g for 10 minutes and the supernatant was transferred to a new tube. Chloroform (200 µl) was added to the solution and incubated for 5 minutes at room temperature. Tubes were again centrifuged at 12000 g for 15 minutes and the upper aqueous phase was transferred to a new tube. One volume of 70% ethanol (v/v) was added and applied to an RNeasy mini spin column (Quiagen, Hilden, Germany). The RNA was washed and eluted according to the manufacturer's protocol. The RNA samples were reverse transcribed into cDNA using oligo (dT)-selection according to the manufacturer's protocol (Superscript Preamplification System, Life Technologies, Gaithersburg, Md.). Osteopontin, bone sialoprotein, and bone morphogenic protein 2 gene expression were quantified using the ABI Prism 7000 Real Time PCR system (Applied Biosystems, Foster City, Calif.). PCR reaction conditions were 2 min at 50° C., 10 min at 95° C., and then 50 cycles at 95° C. for 15 s, and 1 min at 60° C. The expression data were normalized to the expression of the housekeeping gene, glyceraldehyde-3-phosphate-dehydrogenase (GAPDH). The GAPDH probe was labelled at the 5' end with fluorescent dye VIC and with the quencher dye TAMRA at the 3' end. Primer sequences for the human GAPDH gene were: Forward primer 5'-ATG GGG AAG GTG AAG GTC G-3' (SEQ ID NO: 4), reverse primer 5'-TAA AAG CCC TGG TGA CC-3' (SEQ ID NO: 5), probe 5'-CGC CCA ATA CGA CCA AAT CCG TTG AC-3' (SEQ ID NO: 6). Primers and probes for osteopontin, bone sialoprotein (BSP), and bone morphogenic protein 2 (BMP-2) were purchased from Applied Biosciences (Assay on Demand # Hs00167093 ml (osteopontin), Hs 00173720 ml (BSP), Hs 00214079 ml (BMP-2)).

Histology and Microcomputrized Tomography (µ-CT)

For histology, scaffolds were dehydrated, embedded in paraffin and cut in 5 µm sections were. To stain for cartilage differentiation in the pellet culture (FIG. 12), sections were treated with eosin for 1 min, fast green for 5 min, and 0.2% aqueous safranin O solution for 5 min, rinsed with distilled water, dehydrated through xylene, mounted, and placed under a coverslip (Rosenberg, L. 1971. *J Bone Joint Surg Am* 53:69-82).

For the visualization of bone distribution, scaffolds were analyzed using a µCT20 imaging system (Scanco Medical, Bassersdorf, Switzerland) providing a resolution of 34 µm in the face and 250 µm in the cross direction of the scaffold. A constrained Gaussian filter was used to suppress noise. Mineralized tissue was segmented from non-mineralized tissue using a global thresholding procedure. All samples were analyzed using the same filter width (0.7), filter support (Lysaght et al. 1998. *Tissue Eng* 4:231-238), and threshold (195/190) as previously described (Muller et al. 1994 *Phys Med Biol* 39:145-164).

X-Ray Diffraction Measurement (XRD)

X-ray diffraction patterns of scaffolds before and after bone formation were obtained by means of Bruker D8 Discover X-ray diffractometer with GADDS multiwire area detector. WAXD (wide angle X-ray diffraction) experiments were performed employing CuKa radiation (40 kV and 20 mA) and 0.5 mm collimator. The distance between the detector and the sample was 47 mm.

Statistical Analysis

Statistical analysis of data was performed by one-way analysis of variance (ANOVA) and Tukey-Kramer procedure for post hoc comparison using SigmaStat 3.0 for Windows. p values less than 0.05 were considered statistically significant.

Results

Characterization of Human Bone Marrow Stem Cells

The BMSCs exhibited a spindle shaped and fibroblast-like morphology (FIG. 12A). To assess the differentiation potential of the expanded cells, both chondrogenic and osteogenic inducement was studied. The chondrogenic potential of P2 cells was evidenced by evenly red stained areas indicating GAG deposition in the center of the pellets (FIG. 12B). Pellets incubated with either control or osteogenic medium showed no red staining (insert in FIG. 12C). These findings were corroborated by the analysis of sulphated GAG content per unit DNA for chondrogenic differentiation of P1, P3, and P5 cells (FIG. 12E). No statistical difference was observed among the passages. Osteogenic potential of the cells was demonstrated by the spatially uniform deposition of calcified matrix (FIG. 12F). In contrast, pellets incubated in control medium or chondrogenic medium did not show any black or dark brown staining, thus indicating the absence of mineralization. Calcium content per unit DNA was analyzed to quantify the histological observations for osteogenic differentiation for P1, P3, and P5 cells (FIG. 12H). P1 and P3 cells deposited significantly more calcium per DNA than P5 cells ($p<0.05$). BMSCs underwent chondrogenic differentiation only when cultured in chondrogenic medium and osteogenic differentiation only when cultured in osteogenic medium.

Scaffolds, Biochemical Analysis and Real Time RT-PCR

The porosity of the 3D silk matrices was 98%, compressive stress was 170±20 kPa and compressive modulus 450±170 kPa (Nazarov et al. 2003. In *Department of Biomedical Engineering*. Medford: Tufts University).

Figure 13A:
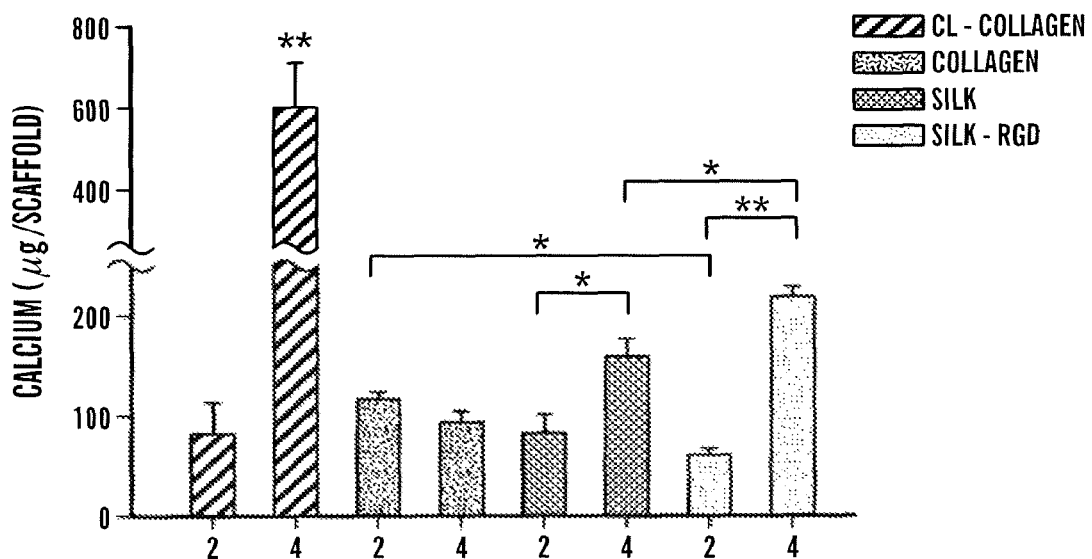
FIGS. 13A and 13B show biochemical characterization of BMSC differentiation on cross linked collagen, collagen, silk, and silk-RGD scaffolds after 2 and 4 weeks in osteogenic culture medium. (13A) Calcium deposition per scaffold and (13B) alkaline phosphatase (AP) activity per scaffold. Data are represented as the average±standard deviation of 3-4 constructs and asterisks indicate statistically significant differences ($p<0.05$=*; $p<0.01$=**).

Calcium deposition was analyzed after 2 and 4 weeks in culture (FIG. 13A). Calcium content decreased on collagen, which was accompanied with advanced biodegradation and resulted in a wet weight of approximately 17% of the initial weight after 4 weeks as described before (Meinel et al. 2003. *Ann Biomed Eng* accepted). Cross linked (CL) collagen scaffolds remained stable with a wet weight of 90±5% after 4 weeks in culture. Calcium deposition was significantly higher when compared to all other groups ($p<0.01$) and approximately 3 times more than compared to silk and silk-RGD and 6 times more than the non CL collagen. A comparison of the non cross linked scaffold material showed that significantly more calcium was deposited on collagen than on silk-RGD matrices after 2 weeks in culture ($p<0.05$). In contrast, BMSCs deposited significantly more calcium on silk ($p<0.05$) and silk-RGD ($p<0.02$) scaffolds as on collagen after 4 weeks. Significantly more calcium was deposited on silk-RGD than on silk scaffolds after 4 weeks ($p<0.05$).

Figure 13B:
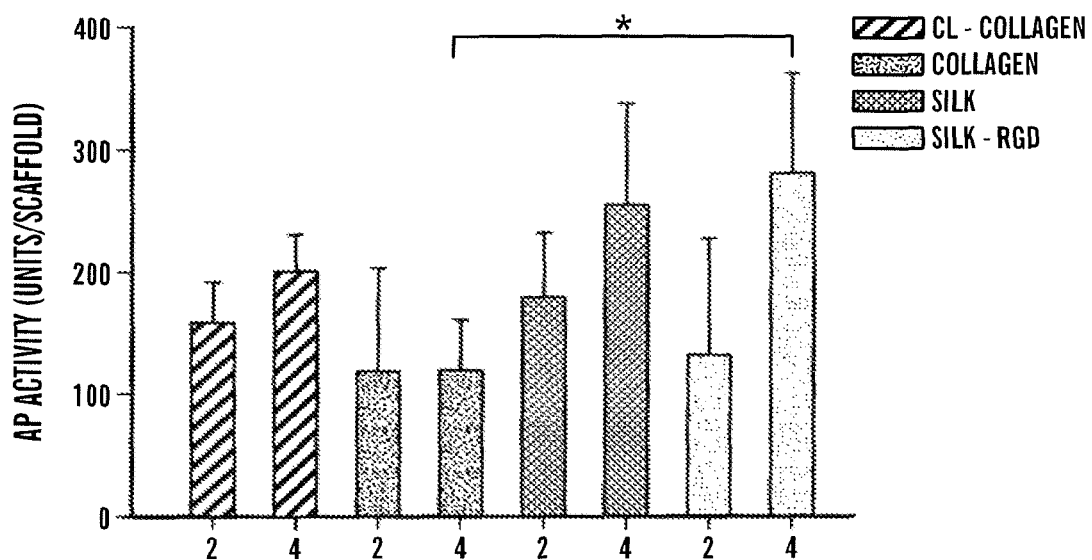

Alkaline phosphatase (AP) activity was variable among the groups as indicated by large standard deviations and statistically not significant differences (FIG. 13B). AP activity was only significantly higher on silk-RGD scaffolds when compared to collagen after 4 weeks in culture ($p<0.05$).

Figure 14A:
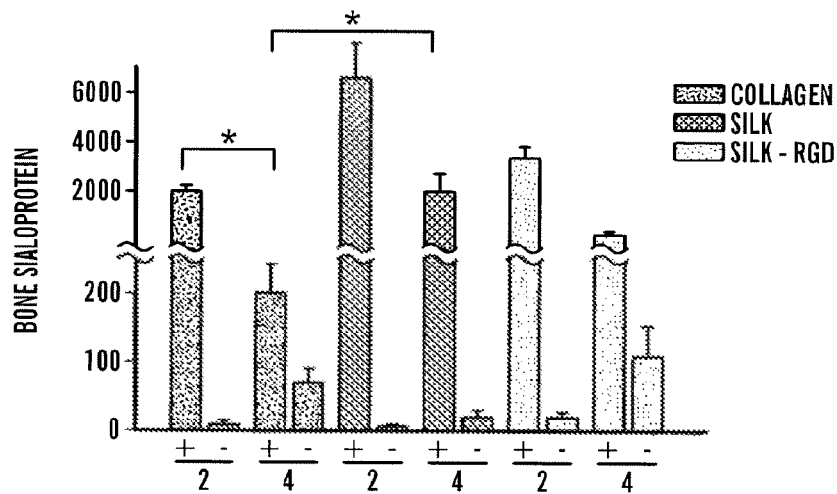
FIGS. 14A-C show gene expression by cells cultured on collagen, silk, and silk-RGD matrices in osteogenic medium (+) and control medium (−) after 2 and 4 weeks in culture. (14A) expression of bone sialoprotein, (14B) osteopontin, and (14C) BMP-2. Data are shown relative to the expression of the respective gene in BMSCs prior to seeding and is the average±standard deviation of 3-4 constructs.

Gene expression of bone sialoprotein (BSP) was upregulated 2000 fold on the collagen scaffolds cultured in osteogenic medium for 2 weeks when compared to the expression by BMSCs prior to seeding (represented by the baseline). When compared to 4 weeks on collagen scaffolds, significantly more BSP transcript was found on collagen after 2 weeks than after 4 weeks in osteogenic medium ($p<0.05$) (FIG. 14A). Gene expression in osteogenic medium was regulated similarly on the silk, and silk-RGD scaffolds, however the decline in transcripts after 4 weeks when compared to 2 weeks was not statistically significant. BSP expression was higher on silk than on collagen scaffolds after 4 weeks in osteogenic medium ($p<0.05$). Scaffolds cultured in control medium were not statistically different from the BMSCs prior to seeding (represented by the baseline).

Figure 14B:
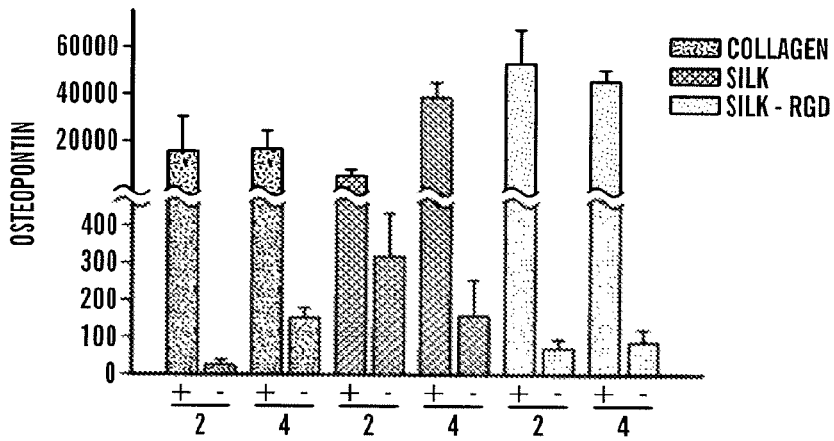

Osteopontin was over-expressed on all scaffolds cultured in osteogenic medium and was similar after 2 and 4 weeks in culture, except for silk, where transcript levels increased, however this observation was not statistically significant (FIG. 14B). Osteopontin expression by all scaffolds cultured in control medium was statistically insignificant from the transcript levels measured in BMSCs prior to seeding of each time point (represented by the baseline).

Figure 14C:
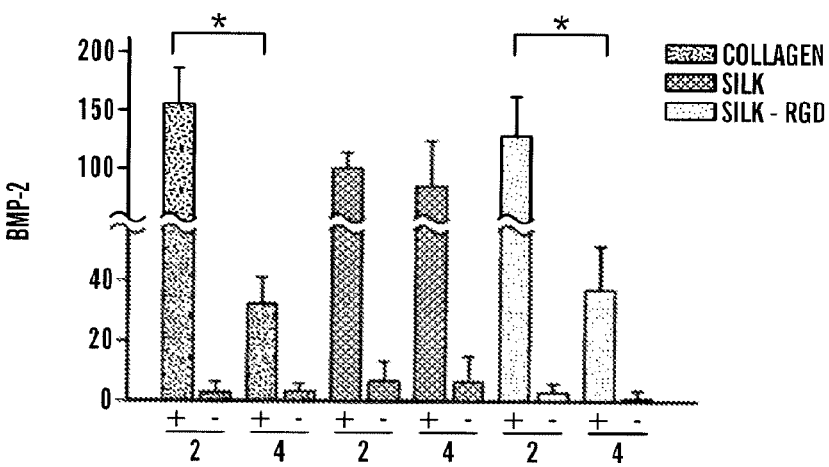
Figure 15A:
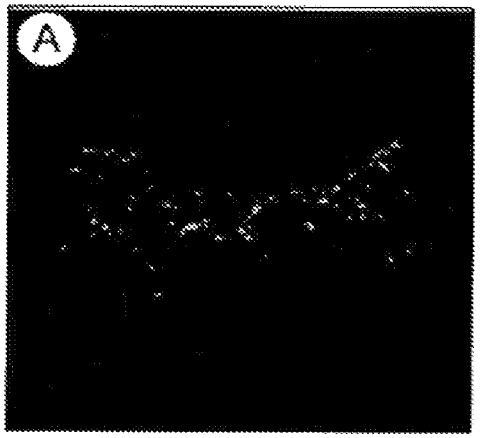
FIGS. 15A-D show µ-CT images taken from collagen (15A, 15B), and silk-RGD scaffolds (15C, 15D). Insert in 15C is a magnification from 15D. Bar length=1.1 mm.
Figure 15B:
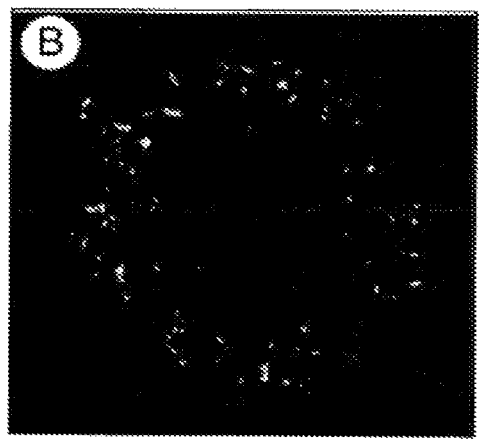
Figure 15C:
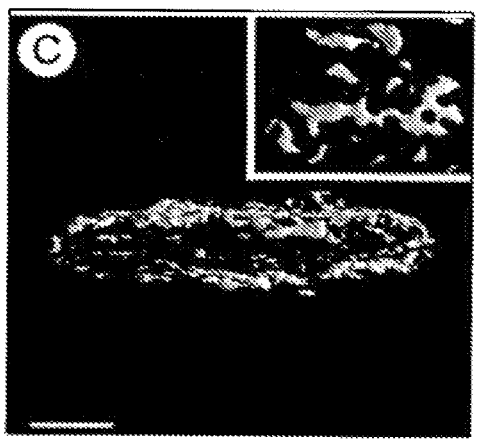
Figure 15D:
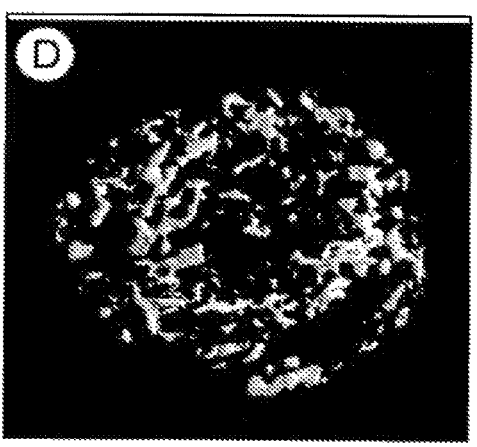

Bone morphogenetic protein 2 (BMP-2) expression was 100-150 fold upregulated after 2 weeks on all scaffolds cultured in osteogenic medium compared to the BMSCs prior to seeding (FIG. 14C). Fewer transcripts were found after 4 weeks on collagen and silk-RGD ($p<0.05$) but not on silk. The expression of BMP-2 was insignificant for all scaffolds in control medium when compared to the expression by BSMCs prior to seeding (represented by the baseline).

Histogenesis of Bone-Like Tissue

After 2 weeks, mineralized spots were observed on the collagen lattice as seen with von Kossa staining. Degradation of the collagen scaffold was advanced and the matrix did not provide a stable lattice. Open areas of the lattice were filled with randomly oriented collagen-like bundles as seen in H&E staining intermingled with fibroblasts. Restricted to certain locations, enlarged cuboidal cells with an osteoblast-like morphology were observed. After 4 weeks, calcification on silk scaffolds was advanced and found adjacent to the scaffold material. Mineralization occurred in locations which coalesced and formed clusters of mineralized matrix (FIG. 12C). Fewer cells were present after 4 weeks when compared to 2 weeks and cells with fibroblast morphology along with cells with osteoblast like morphology were observed.

Mineralization on silk was appositional to the scaffold lattice and occurred in distinct spots (FIG. 12E). The void areas of the matrix were filled with randomly oriented collagen-like fibres and some fibroblasts and osteoblast like cells were found, predominantly adjacent to the silk. After 4 weeks, deposition was advanced, especially at the border zones of the silk. Changes in the extracellular matrix were observed confined to restricted areas (approx. 50×50 µm) with parallel oriented collagen bundles surrounded by areas with randomly oriented collagen bundles. Increased numbers of osteoblast like cells with a cuboidal or columnar morphology were observed and some of the cells were in contact via short processes.

On silk-RGD matrices, mineralization occurred in a mode similar to the silk matrix, appositional to the scaffold lattice. After 2 weeks in osteogenic medium, the void scaffold area was completely filled with connective tissue, comprised of randomly oriented collagen-like fibres, fibroblasts and cuboidal osteoblast-like cells which were connected via cellular processes. After 4 weeks, mineralization was especially advanced on the silk-RGD scaffolds compared to silk and collagen. Aside from the small areas that do not stain, a calcified matrix covered the entire silk-RGD lattice. The void area between the lattices was completely filled with extracellular matrix, consisting of parallel oriented collagen bundles, osteoblast like cells, and few cells with fibroblast like morphology. The cells seemed to be interconnected via long processes.

Bone deposition was imaged after 4 weeks in osteogenic medium with micro-computerized tomography (µ-CT) of randomly selected collagen and silk-RGD scaffolds (FIG. 15). Mineralized and unconnected clusters were distributed mainly at the outer rim of the collagen constructs (FIG. 15B). Biodegradation was visible by the concave shape of the scaffold and a decrease in diameter and thickness by approximately 30% from the original shape (FIG. 15A). No image data were collected for the silk scaffold as mineralization was below the threshold level chosen for the µ-CT imaging. The silk-RGD scaffold showed advanced calcification. Bone deposition was present at the top and bottom and not in the center of the scaffold. The scaffold size remained unchanged during the experiment indicating no substrate degradation during the time frame of the experiment (FIG. 15C). The calcified rods formed up to 1.2×0.4×0.2 mm (length×width×thickness) interconnected lattices. These interconnected lattices formed trabecular like geometries, encircling hexagonal voids (not calcified) areas (FIG. 12D, and insert 12C). To identify the bone like nature of the deposited bone tissue, we compared X-ray diffraction patterns of poorly crystalline hydroxyapatite (p.c. HA) as predominantly present in bone (Harper et al. 1966. *Proc Soc Exp Biol Med* 122:137-142) and the engineered tissue. Basically, diffracted X-rays from the tissue engineered bone like tissue on silk, collagen, CL-collagen (data not shown) and silk-RGD were the same as of the p.c. HA. The peak observed at 20° in the tissue engineered bone resulted from the silk-RGD scaffold, as determined by a comparison with the XRD pattern of the plain scaffold.

Discussion

In recent years substantial progress has been achieved in the tissue engineering of human autologous bone grafts (Petite et al. 2000. *Nat Biotechnol* 18:959-963; Athanasiou et al. 2000. *Tissue Eng* 6:361-381; Kale et al. 2000. *Nat Biotechnol* 18:954-958; Niklason, L. E. 2000. *Nat Biotechnol* 18:929-930; Schoeters et al. 1992. *Cell Prolif* 25:587-603). To evaluate the potential of silk as a scaffold for bone tissue engineering mesenchymal stem cells (BMSC) derived from human bone marrow were cultured in three different 3D porous scaffolds (silk, silk-RGD, and collagen) to study osteogenesis under controlled in vitro conditions. BMSCs cultured on the protein scaffolds for up to four weeks formed mineralized bone matrix, and the amount, density, and structure of bone matrix depended on scaffold degradation and scaffold decoration with RGD.

Human mesenchymal stem cells are a source for autologous bone tissue engineering. They proliferate and differentiate in vitro, can be easily isolated from bone marrow aspirates, and have a documented potential for osteogenic and chondrogenic differentiation (Friedenstein, A. J. 1976. *Int Rev Cytol* 47:327-359; Friedenstein et al. 1987. *Cell Tissue Kinet* 20:263-272; Caplan, A. I. 1994. *Clin Plast Surg* 21:429-435; Pittenger et al. 1999. *Science* 284:143-147). The osteogenic pathway has been proposed to be the default lineage of this population of cells (Banfi et al. 2002. *Tissue Eng* 8:901-910). The isolated and expanded BMSCs were positive for the putative BMSC marker CD105/endoglin (Barry et al. 1999. *Biochem Biophys Res Commun* 265:134-139), and had a capacity for selective differentiation into either cartilage- or bone-forming cells (FIG. 12E). The expanded cells could be induced to undergo either chondrogenic or osteogenic differentiation via medium supplementation with chondrogenic or osteogenic factors, respectively (FIGS. 12B, 12C & 12F, 12G). No notable difference in cell differentiation capacity over 3 passages in culture was observed, however calcium deposition of passage 5 cells was significantly reduced when compared to passage 1 and 3 cells (FIGS. 12D & 12H). In conclusion, the isolated P2 BMSCs used in this study retained osteogenic and chondrogenic differentiation potential which made them a suitable cell source for bone tissue engineering.

Scaffold chemistry and surface modification had a significant impact on mineralization of the matrices. Total calcium deposition per scaffold was advanced on collagen scaffolds, but declined after 4 weeks. This effect was correlated with the biodegradation of the collagen scaffold (Meinel et al. 2003. *Ann Biomed Eng* accepted). Ideally, a scaffold would provide a suitable mechanical match until gradually replaced by the newly deposited bone. Bone deposition was already present after 2 weeks in culture (FIG. 13A) however, the biodegradation of collagen was too rapid to allow a substantial and stable replacement with newly formed bone. Histological evaluation demonstrated a progression in bone deposition of the collagen scaffolds between week 2 and 4, although total calcium per scaffold decreased due to biodegradation. The collagen used in this study did not retain its structure leading to collapsed collagen fragments intermingled with connective tissue. Presumably, the eroding frame did not allow the bone clusters to connect and, therefore, randomly distributed mineralized clusters were scattered mainly at the rim of the scaffold also leading to transport limitations in the center of the collapsed structure (FIG. 15). To understand the significance of biodegradation on the decline in calcium content on collagen scaffolds after 4 versus 2 weeks, cross linked (CL) collagen scaffolds were prepared, in which biodegradation was reduced (Carpentier et al 1969 *J. Thorac Cardiovsc Surg* 58:467-483). The CL-collagen did not show substantial degradation, whereas the natural polymer degraded and wet weight after 4 weeks in culture was about 5 times less as the initial weight. Similarly, calcium content on the CL-collagen was 6 times higher as compared to the untreated and natural polymer (FIG. 13). This suggests that the observed loss in calcium content on the natural collagen was mainly due rapid degradation of the scaffold. Collagen scaffolds prepared by physical processes resemble more the natural collagen and have less cytotoxic effects and better biocompatibility when compared to chemically cross-linked materials (van Luyn et al. 1992. *J Biomed Mater Res* 26:1091-1110). Furthermore silk based materials can cover a broader range of mechanical properties than collagen based materials, which may be a substantial advantage to meet physiological needs at the implantation site (Altman et al. 2003. *Biomaterials* 24:401-416). Because of these constraints and the focus of this study to compare natural polymers, only physically stabilized scaffolds were further characterized and described in this study.

The introduction of RGD moieties by covalent decoration of the silk surfaces resulted in significantly increased calcium deposition in comparison to non decorated silk or the collagen (FIG. 13A). This is in accordance with previous studies using silk films decorated with RGD (Sofia et al. 2001. *J Biomed Mater Res* 54:139-148). Interestingly, bone formation on silk-RGD scaffolds was organized resulting in interconnected trabeculae of bone like tissue (FIG. 15). The trabeculae encircle hexagonal void areas, which were in the range of the pore sizes of the silk scaffolds. Histological evaluation corroborated this evidence, and new bone like tissue was deposited appositionally to the silk scaffold lattice. These data suggest that the silk scaffold geometry may predetermine the geometry of the engineered bone. Calcium deposition was mainly on the top and bottom of the scaffold. Similar to most previous studies, it is likely that diffusional limitations associated with mass transport have limited successful efforts to engineer compact and continuous bone structures (Ishaug et al. 1997. *J Biomed Mater Res* 36:17-28; Martin et al. 2001. *J Biomed Mater Res* 55:229-235). A possible avenue to overcome these limitations are bioreactors. Bioreactors support the supply of oxygen, nutrients, metabolites, and regulatory molecules and facilitate mass transfer to the center of the scaffolds (Freed et al. 2000. In *Principles of Tissue Engineering*. R. P. Lanza, R. Langer, and J. Vacanti, editors. San Diego: Academic Press. 143-156). Since silk biodegradation is slow the scaffolds provide a robust network likely to withstand medium flow conditions (laminar or turbulent flow used in most bioreactors) without loss of mechanical integrity.

To characterize the nature of the mineralized tissue, XRD patterns of engineered bone like tissue were compared to poorly crystalline hydroxyapatite (p.c. HA). From early diffraction measurements it was concluded, that bone mineral is a two phase system, one of which was p.c. HA and the other an amorphous calcium phosphate which makes up less than 10% of the mineralized bone (Betts et al. 1975. *Proc Natl Acad Sci USA* 72:2088-2090). However, more recent studies could not detect amorphous calcium phosphate even in embryonic bone (Bonar et al. 1984. *J Ultrastruct Res* 86:93-99; Grynpas, M. D., et al. 1984. *Calcif Tissue Int* 36:291-301). The similarity in XRD patterns between p.c. HA and the engineered tissue suggested the bone like nature of the deposited interconnected trabeculae.

Substantial differences in the organization of the extracellular matrix were observed on the silks between 2 and 4 weeks in osteogenic medium. After 4 weeks dense connective tissue filled the voids of the silk and silk-RGD lattice in which cuboidal osteoblast like cells were in contact with one another via long tapering processes. The intercellular space was occupied with organized bundles of collagens. This was accompanied by strong induction of gene expression for a non-collagenous element of the extracellular matrix, bone sialoprotein (BSP) (FIG. 14). BSP constitutes about 15% of the non-collagenous proteins found in the mineralized compartment of young bone and supports cell attachment through both RGD dependent and RGD-independent mechanisms, with a high affinity for hydroxyapatite (Fisher et al. 1983. *J Biol Chem* 258:12723-12727). The strong up-regulation of both genes in response to BMP-2 has been reported in previous studies (Lecanda et al. 1997. *J Cell Biochem* 67:386-396; Zhao et al. 2003. *J Dent Res* 82:23-27). The upregulated expression of BSP reflects the strong induction of extracellular matrix protein production which is seen in the histological sections. Osteopontin expression was similarly increased after 2 and 4 weeks on all scaffolds. Osteopontin regulates cell adhesion, migration, survival, and calcium crystal formation, playing a role in biomineralization and early osteogenesis (Butler, W. T. 1989. *Connect Tissue Res* 23:123-136). Therefore, the increased expression of osteopontin corroborates the advanced mineralization progress evident after 2 weeks in culture.

In summary, tissue engineered organized and trabecular bone-like morphologies were obtained by using BMSCs cultured in osteogenic medium on 3D silk scaffolds. This was accompanied by the production of an organized extracelular matrix. The decoration of silk scaffolds with RGD sequences resulted in increased calcification and a more structured extracellular matrix. Collagen scaffolds could not generate similar outcomes due to the rapid rate of degradation. Large tissue engineered bone with an organized geometry on natural non cross linked polymers can be engineered by cultivation of BMSCs seeded on silk-RGD scaffolds in conjunction with bioreactors.

Example IV

Scaffold Geometry Can Determine Tissue Geometry

Tissue engineered bone was produced on silk material scaffolds that were prepared as described herein. Several scaffolds were prepared with mean pore sizes of 106 microns, 225 microns, and 425 microns.

Scaffolds were seeded with $5\times10^6$ human mesenchymal stem cells and cultured in osteogenic medium as described in Example III for up to 5 weeks in a spinner flask. Use of the spinner flask created a turbulent flow of medium around the scaffolds. Bone growth was monitored by pt-computed tomography, the results of which are shown in FIGS. 16A-16I. FIG. 16A-16I shows tissue engineered bone on three silk scaffolds with mean pore sizes of 106 μm (16A, 16D, 16G), 225 μm (16B, 16E, 16H), and 425 μm (16C, 16F, 16I). The first row shows a face view, second row a lateral view and third row a magnification taken from 16A-16C. The data demonstrates, that plate like bone can be engineered on the scaffolds with small pore sizes (16A, 16D, 16G), and trabecular structure and organization can be pre-determined by scaffold geometry. 16J-16L show scaffolds prior to tissue culture of a mean pore size of 106 μm (16J), 225 μm (16K), and 425 μm (16L).

All references cited herein and throughout the specification are herein incorporated by reference in their entirety.

The invention claimed is:

1. A method of preparing a porous article comprising silk fibroin, the method comprising: (a) casting a solution comprising silk fibroin into a mold, wherein the mold contains a water soluble porogen; (b) removing solvent from the solution in the mold, thereby forming a porogen/silk fibroin composite; and (c) leaching out the porogen from said porogen/silk fibroin composite.

2. The method of claim 1, wherein the porogen is mixed in the silk fibroin solution before casting.

3. The method of claim 1, wherein the porogen is selected from NaCl, ammonium bicarbonate, alkali metals, alkali earth metal halides, phosphates, sulfates, sugar crystals, water soluble microspheres, polysaccharides, and protein microspheres.

4. The method of claim 1, wherein said removing the solvent comprises sublimation or evaporation.

5. The method of claim 1, the method further comprising inducing a conformational change in the silk fibroin to a beta-sheet and insolubility in aqueous solution before leaching out the porogen.

6. The method of claim 1, wherein the solution comprises hexafluoroisopropanol (HFIP).

7. The method of claim 1, wherein weight ratio of porogen to silk fibroin is 10:1 to 20:1.

8. A method of preparing a porous article comprising silk fibroin, the method comprising: (a) casting a mixture of silk fibroin/alcohol/water into a mold; and (b) freeze-drying the mixture in the mold.

* * * * *